United States Patent
Jalali et al.

(10) Patent No.: US 12,318,663 B1
(45) Date of Patent: Jun. 3, 2025

(54) SYSTEM AND METHOD FOR AUTOMATED DIAGNOSIS OF MUSCULOSKELETAL AND NEUROLOGICAL DISORDERS

(71) Applicant: iMagine Design LLC, Tuscon, AZ (US)

(72) Inventors: Bahram Jalali, Los Angeles, CA (US); William R Ryan, Los Angeles, CA (US)

(73) Assignee: iMagine Design, LLC, Tuscon, AZ (US)

( * ) Notice: Subject to any disclaimer, the term of this patent is extended or adjusted under 35 U.S.C. 154(b) by 0 days.

(21) Appl. No.: 18/958,326

(22) Filed: Nov. 25, 2024

(51) Int. Cl.
  A63B 24/00 (2006.01)
  A61B 5/00 (2006.01)
  (Continued)

(52) U.S. Cl.
  CPC ........ *A63B 24/0075* (2013.01); *A61B 5/0077* (2013.01); *A61B 5/0205* (2013.01);
  (Continued)

(58) Field of Classification Search
  CPC . A61B 5/1101; A61B 2505/09; A61B 5/4082; G06T 7/13
  See application file for complete search history.

(56) References Cited

U.S. PATENT DOCUMENTS

2018/0177436 A1* 6/2018 Chang ................. A61B 5/1101
2021/0145359 A1* 5/2021 Hunt .................... A61B 5/4836
(Continued)

OTHER PUBLICATIONS

Zhang, H., Pose-based tremor type and level analysis for Parkinson's disease from video, Int J Comput Assist Radiol Surg., Jan. 18, 2024; 19(5):831-840 (Year: 2024).*
(Continued)

*Primary Examiner* — Dmitry Suhol
*Assistant Examiner* — Alyssa N Brandley
(74) *Attorney, Agent, or Firm* — Mark R Kendrick

(57) ABSTRACT

A method comprising to analyze the captured video data of the patient's body parts and to generate patient motion metrics, patient posture metrics, and patient gait metrics for each exercise routine completed by the patient based on the analyzed video data; store, in a database, the generated patient motion metrics, the patient posture metrics and the patient gait metrics for each of the completed exercise routines, wherein the generated patient motion metrics, the generated patient posture metrics and the generated patient gait metrics are used to track patient progress during physical therapy sessions, diagnose movement disorders, and provide personalized, data-driven treatment plans to enhance immediate outcomes and long-term recovery with respect to the musculoskeletal and neurological disorders; apply motion amplification algorithms to enhance the additional video data to provide clarity of tremor movements; apply edge detection to enhance tremor movement boundaries and detection; generate tremor amplitude measurements and tremor frequency measurements based on the motion amplification and edge detection algorithms; and store, in the database, the generated tremor amplitude measurements and tremor frequency measurements, wherein the generated tremor amplitude measurements and tremor frequency measurements are analyzed for diagnosis and monitoring of disorders such as Parkinson's disease and Essential Tremor.

18 Claims, 15 Drawing Sheets

(51) Int. Cl.
*A61B 5/0205* (2006.01)
*A61B 5/103* (2006.01)
*A61B 5/107* (2006.01)
*A61B 5/11* (2006.01)
*A61B 5/1455* (2006.01)
*A61B 5/397* (2021.01)
*A61B 7/00* (2006.01)
*A63B 71/06* (2006.01)
*G06T 7/00* (2017.01)
*G06T 7/13* (2017.01)

(52) U.S. Cl.
CPC .......... *A61B 5/1101* (2013.01); *A61B 5/1128* (2013.01); *A61B 5/7267* (2013.01); *A63B 71/0622* (2013.01); *G06T 7/0016* (2013.01); *G06T 7/13* (2017.01); *A61B 5/1036* (2013.01); *A61B 5/1077* (2013.01); *A61B 5/1079* (2013.01); *A61B 5/14552* (2013.01); *A61B 5/397* (2021.01); *A61B 5/4082* (2013.01); *A61B 5/4561* (2013.01); *A61B 5/486* (2013.01); *A61B 7/006* (2013.01); *A61B 2505/09* (2013.01); *A61B 2562/0219* (2013.01); *G06T 2207/10016* (2013.01); *G06T 2207/20081* (2013.01); *G06T 2207/30004* (2013.01)

(56) References Cited

U.S. PATENT DOCUMENTS

| | | | |
|---|---|---|---|
| 2022/0031199 A1* | 2/2022 | Hao | G16H 50/70 |
| 2022/0296129 A1* | 9/2022 | Dodemont | A61B 5/053 |
| 2023/0000396 A1* | 1/2023 | Coffey | A61B 5/1117 |
| 2024/0260892 A1* | 8/2024 | Haas | A61B 5/4824 |

OTHER PUBLICATIONS

Wang, X., et al., Hand tremor detection in videos with cluttered background using neural network based approaches, Health Inf Sci Syst., Jul. 12, 2021; 9(1):30 (Year: 2021).*

* cited by examiner

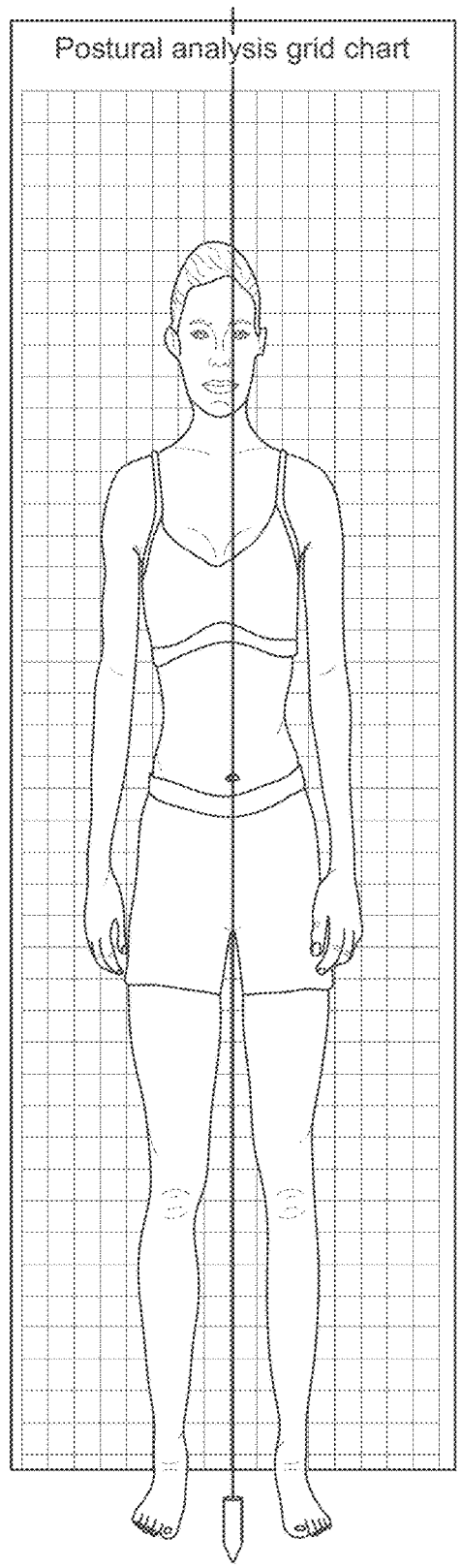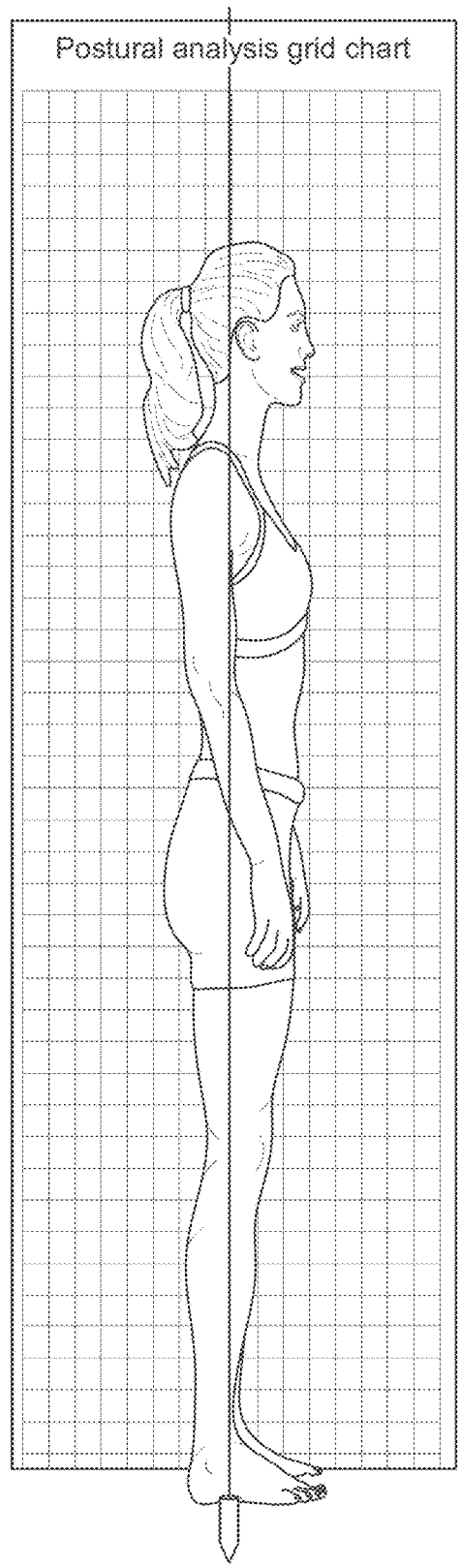
Postural analysis: normal vs abnormal posture
FIG. 2

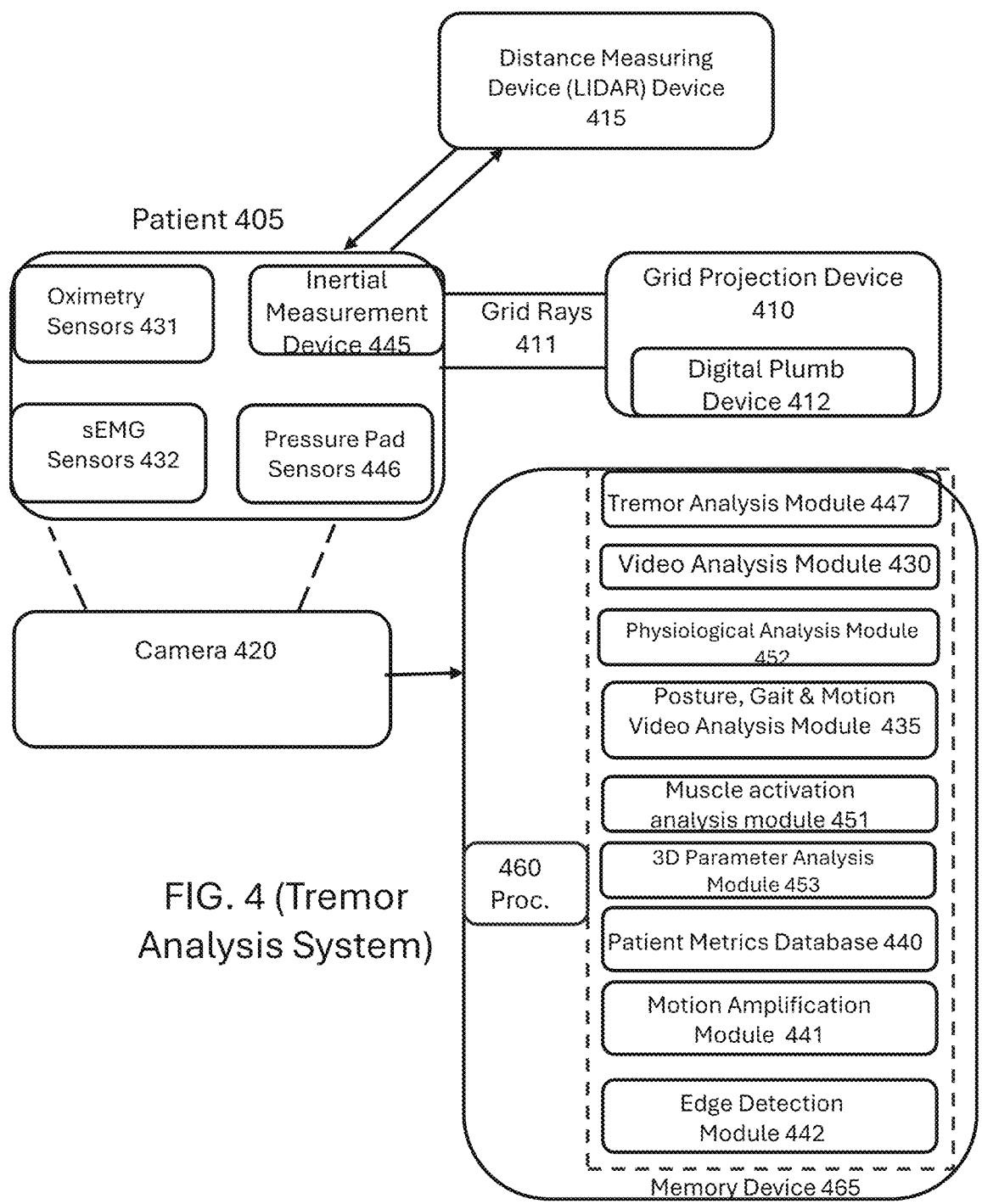
FIG. 4 (Tremor Analysis System)

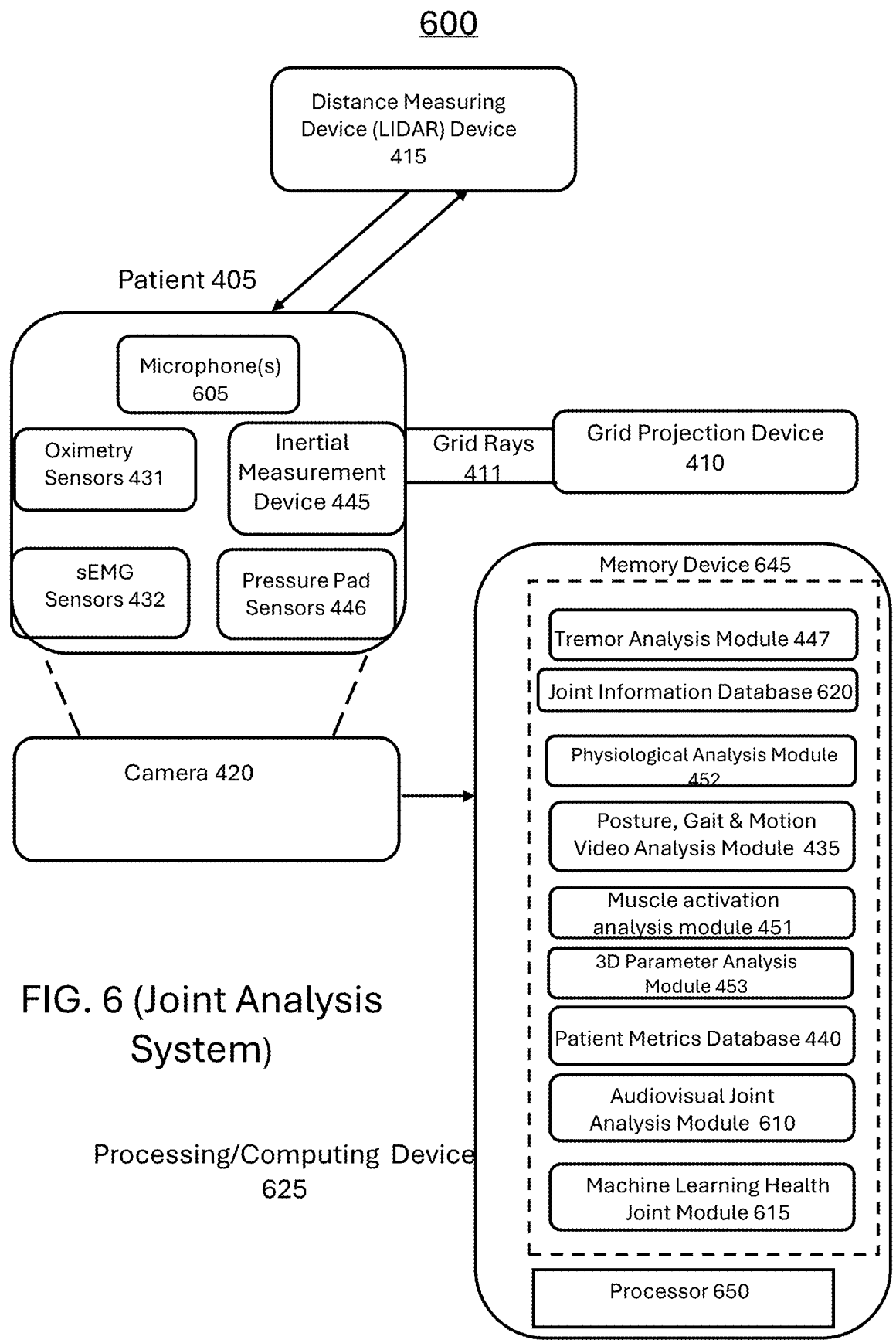
FIG. 6 (Joint Analysis System)

FIG. 8 – Perspective Projection for 3D Mapping System

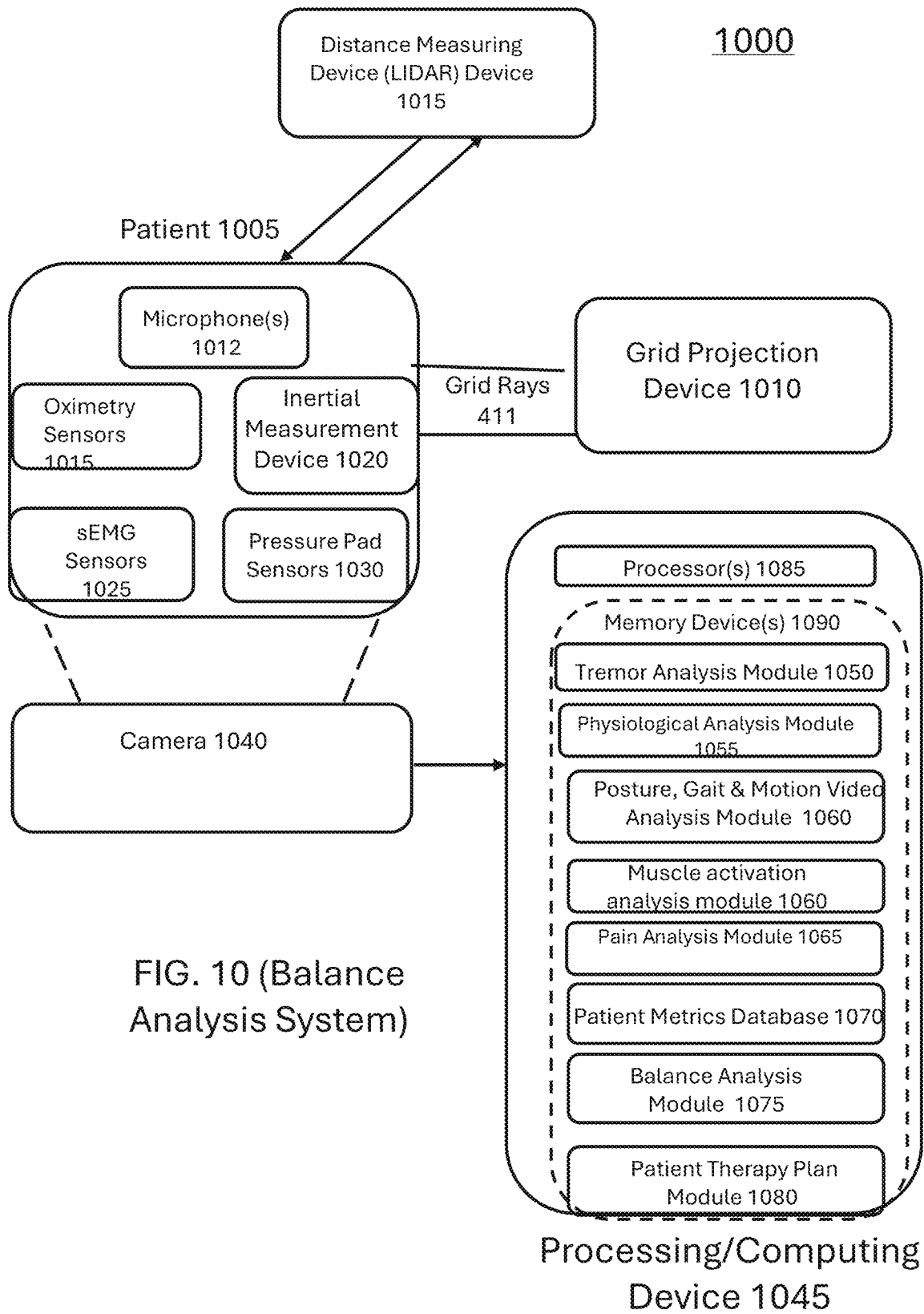
FIG. 10 (Balance Analysis System)

1145 — Therapy plan module may generate or create personalized targeted rehabilitation exercises or exercise adjustments to the patient's current therapy exercise program to improve balance, coordination, and strength based on metrics described above along with the patient's balance parameters and balance assessment

1150 — Therapy plan module may provide real-time feedback and biofeedback to the patient via a patient's computing device during the physical therapy session (or before or after the physical therapy session) to guide the patient in making necessary adjustments for balance improvement

1155 — Therapy plan module may measure an outcome with respect to the various measurements and parameters discussed above based on the adjustments to the physical therapy sessions described above

FIG. 11B

SYSTEM AND METHOD FOR AUTOMATED DIAGNOSIS OF MUSCULOSKELETAL AND NEUROLOGICAL DISORDERS

BACKGROUND

In physical therapy, examining a patient's pose and posture is a fundamental aspect of assessment and treatment. Physical therapists (PTs) use this examination to identify abnormalities, imbalances, or weaknesses that may contribute to pain, dysfunction, or injury. Here's how the PTs utilize pose and posture examination in practice. Initial Assessment-Observation. The PT begins by observing the patient in various static positions (e.g., standing, sitting) and during movement (e.g., walking, bending). They look for asymmetries, such as uneven shoulders, tilted pelvis, or forward head posture. FIG. 2 illustrates a patient postural analysis grid chart according to exemplary embodiments. Reference number 205 illustrates a straight on view or a front view and reference number 210 illustrates a side view. Baseline Posture: The PT may establish a baseline posture helps the PT understand the patient's natural alignment and any deviations from the ideal posture. This can reveal areas of tension or muscle imbalance. A PT may then identify postural deviations. The PT may look for common deviations such as specific postural deviations (kyphosis (excessive curvature of the upper back), lordosis (excessive inward curvature of the lower back), scoliosis (lateral curvature of the spine), and forward head posture). The PT may also look for muscle imbalances, (e.g., where certain muscles may be overly tight or weak), leading to improper alignment or movement patterns. The PT may then perform functional movement analysis. The PT may perform a dynamic assessment where the PT assesses how posture affects movement by observing the patient perform functional tasks like squatting, lifting, or reaching. This helps identify how postural issues may impact everyday activities and contribute to pain or injury. In addition, the PT may perform gait analysis (e.g., observing how the patient walks). This can reveal issues such as overpronation, uneven stride length, or compensatory movements that stem from poor posture.

The PT may also try pain and dysfunction correlation. The PT may attempt to link posture to symptoms. The PT correlates observed postural issues with the patient's reported symptoms. For example, forward head posture might be linked to neck pain or headaches, while a tilted pelvis could be associated with lower back pain. In some cases, the PT may test a hypothesis. By making small adjustments to the patient's posture during the exam, the PT can determine if changes in alignment reduce pain or improve function, helping to confirm the diagnosis.

The PT may then develop a treatment plan for the patient. The PT may come up with corrective exercises. In other words, based on the findings, the PT may design a treatment plan that includes exercises to correct postural imbalances. This might involve stretching tight muscles, strengthening weak muscles, and teaching the patient proper alignment and movement techniques. The PT may also educate the patient on correct posture throughout daily activities, providing tips and exercises to reinforce good posture. Finally, the PT may monitor process. The PT may reassess the patient by re-examining the patient's posture throughout the course of treatment to monitor the outcome of the therapy and make necessary adjustments to the treatment plan. Improvements in posture often correlate with reductions in pain and improvements in function. What is needed is a digital system that allows the PT to make an automated diagnosis of musculoskeletal issues and the longitudinal assessment of subject's progression for physical therapy and sports medicine.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 2 illustrates a patient postural analysis grid chart according to exemplary embodiments;

FIG. 4 illustrates a system for tremor detection and/or visualization according to exemplary embodiments;

FIG. 6 illustrates a block diagram of a joint analysis system according to exemplary embodiments;

FIG. 10 illustrates a block diagram of a balance detection, analysis, and diagnosis system or method according to exemplary embodiments;

FIG. 11B illustrates a flowchart of a method and system for balance detection, analysis, and diagnosis according to exemplary embodiments.

DETAILED DESCRIPTION

Figure 1:
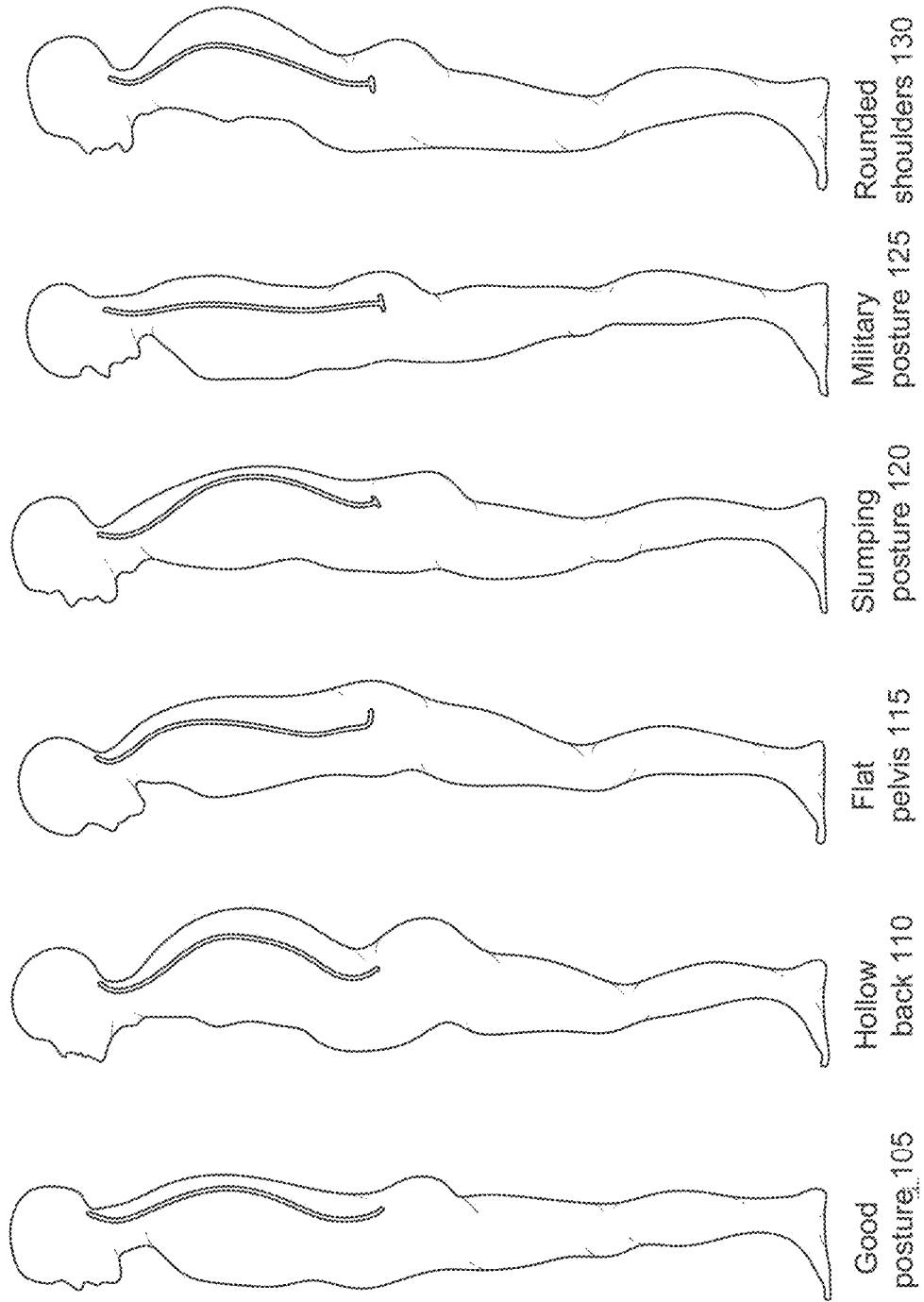
FIG. 1 illustrates postures of a patient which may be utilized for comparison to an actual patient.

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The present subject matter relates to an intelligent and automated system and method for diagnosis, treatment and rehabilitation of musculoskeletal issues and neurological disorders.

The components of the basic system include a plurality of cameras configured to capture videos of the patient's body part combined. This is combined with machine learning algorithms that analyze the captured videos to measure motion and posture and to quantify gait metrics.

The comprehensive system allows physical therapists or sport trainers to track patient progress, diagnose movement disorders, and offer personalized, data-driven treatment plans, enhancing both immediate outcomes and long-term recovery.

In exemplary embodiments, the system may incorporate wearable sensors with surface electromyography (sEMG) technology to measure muscle activation patterns in relation to posture, providing biofeedback to optimize therapeutic interventions. The sEMG sensors provides insight into the muscular contributions to postural problems, which can be essential for creating effective treatment plans.

In exemplary embodiments, the system may also use wearable pulse and oximeter sensors for real-time monitoring and collection of heart rate and blood oxygen and $CO_2$ levels during the physical therapy and rehabilitation exercises.

In exemplary embodiments, the system may integrate an optional wearable inertial measurement unit (IMU) to record 3D acceleration, rotation and/or tilt of the body parts during the exercise (and generate 3D acceleration, rotation and/or tilt parameters or measurements.

In exemplary embodiments, the system and/or method may also include and/or utilize an optional pressure pad or pads on which the patient stands during the prescribed exercises. The pad measures and reports the distribution of weight on patient's feet and generates balance parameters or measurements.

In exemplary embodiments, the system and/or method may include and/or utilize a laser distance/range measurement tool, e.g. a lidar, as a digital curve ruler to scan and record contours of the spine or back (or other body parts), making it suitable for diagnosing conditions such as scoliosis or kyphosis.

In exemplary embodiments, the system and/or method may include a first module (which may be a first system or method for detecting and quantifying tremors or tremor movements in patients with neurological disorders). Specifically, in exemplary embodiments, this tremor analysis module may use video analysis via edge detection, and/or optional motion amplification techniques to measure tremor amplitude and frequency in various body parts, such as the arm, leg, or head, particularly for disorders like Essential Tremor or Parkinson's disease. Tremor detection from video may be performed along with the calculating of posture and gait measurements, which are captured by cameras and then determined via machine learning algorithms or analytics.

In exemplary embodiments, the system may include a second module that performs audiovisual diagnostics of a patient's joints. In exemplary embodiments, the second module may record joint sounds that are synchronized with the video recording of a patient's gait or joint movement to provide a rich audiovisual dataset for diagnosis of a patient's joint health. In exemplary embodiments, the system and method associates with this second module combines the simultaneous recording and quantitative analysis of sound and video of joints during digital physical therapy sessions and then utilizes audio data and visual data for diagnosing the patient's musculoskeletal health.

In exemplary embodiments, the system and/or method may include a third module, wherein the third module includes structured illumination and/or perspective projection for 3D mapping of the patient's body. In exemplary embodiments, the generated patient 3D maps may provide accurate representations of a patient's posture and movement and offer comprehensive insights for diagnosis and treatment planning. In exemplary embodiments, in the third module, with the 3D mapping capability, a digital twin or representation of the patient's body can be created. In exemplary embodiments, in the third module, the 3D model may be curated or combined with gait, pain and tremor measurements or parameters and other measured metrics for a comprehensive assessment of the patient.

In exemplary embodiments, the system and/or method may also include a database that may store the measurement data described above, facilitating the longitudinal study of postural and gait changes (as well as tremor measurements and synchronized audio data and video data of joints) over time, and the efficacy of treatment and rehabilitation for physical therapists and athletic trainers. The system described herein supports both local and cloud storage for efficient data management and processing.

In exemplary embodiments, a balance detection, analysis, and diagnosis system or method is described. The balance detection, analysis and diagnosis system or method may assist patients with diabetes-induced and/or chemotherapy-induced neuropathyIn exemplary embodiments, the system and/or method described herein may have utility in diagnostics and therapy for identifying and treating patients with scoliosis, kyphosis, Parkinson's disease, osteoarthritis, tendonitis, cartilage degeneration and other such disorders. In exemplary embodiments, both the balance screening and training may be facilitated with an intelligent camera and associated balance detection, analysis, and diagnosis system or method to measure, quantify and store quantitative gait and balance data on patients. The balance analysis and diagnosis system's and method's ability to perform detailed posture and gait analysis allows healthcare professionals to assess the specific ways neuropathy affects a patient's movement. In exemplary embodiments, by capturing the patient's movements and analyzing them in real time, clinicians and therapy practitioners may identify balance deficiencies, gait abnormalities, and the severity of neuropathy impacts In exemplary embodiments, the system and method described herein may have applications in diagnosis and quantitative measurement of post-surgery outcome with respect to various surgical operations such as rotator cuff repair, total shoulder arthroplasty, total knee arthroplasty, frozen shoulder, degenerative flat foot and plantar fasciitis and other disorders of foot and ankle.

Figure 5A:
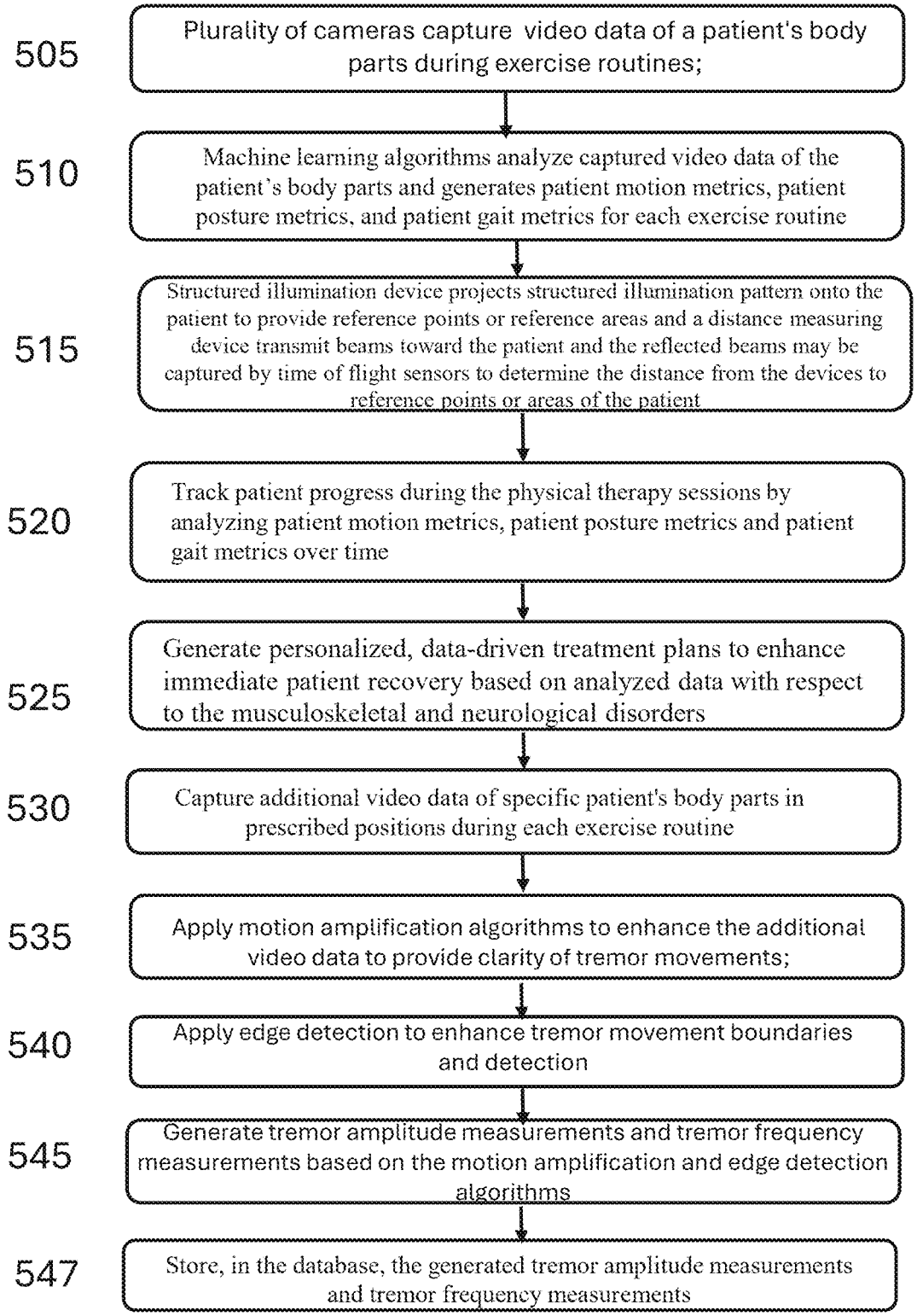
FIGS. 5A and 5B illustrate a flowchart describing a base physical therapy digital system along with a tremor detection, analysis, and/or visualization according to exemplary embodiments.
Figure 5B:
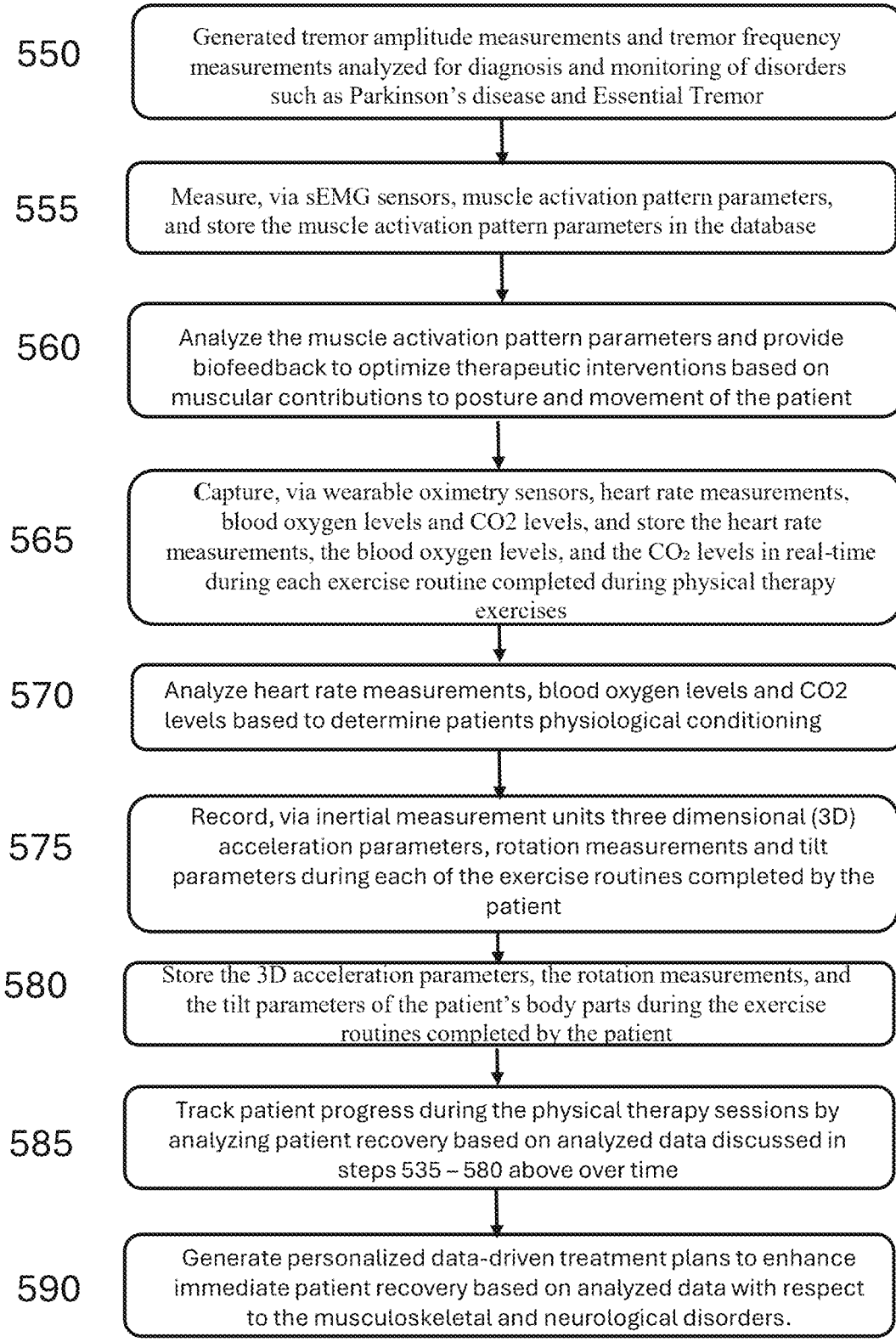

FIG. 4 illustrates a block diagram of a system for tremor detection and/or visualization according to exemplary embodiments. FIGS. 5A and 5B illustrate a flowchart describing a base physical therapy digital system and/or method along with a tremor detection, analysis, and/or visualization system and/or method according to exemplary embodiments. The present enhancement and subject matter described herein relates to systems and methods for detecting and quantifying tremors in patients. Specifically, it pertains to using video analysis, edge detection, and/or motion amplification techniques to measure tremor amplitude and/or frequency in various body parts, such as the arm, hand, leg, or head, particularly for disorders like Parkinson's disease. Tremors are a common symptom in various neurological disorders, including Parkinson's disease. Accurate measurement of tremor characteristics is crucial for diagnosis, treatment planning, and monitoring disease progression. Traditional methods of tremor assessment lack precision or fail to provide real-time, quantifiable data. Accordingly, there is a need for an advanced system that integrates modern technology to provide accurate and comprehensive tremor analysis. The subject matter provides a sophisticated system for detecting and quantifying tremors in a patient's body part using advanced video analysis techniques. In exemplary embodiments, the system and/or method may be designed to capture, analyze, and quantify tremor movements with high precision, edge detection, and optional motion amplification methods.

Figure 3A:
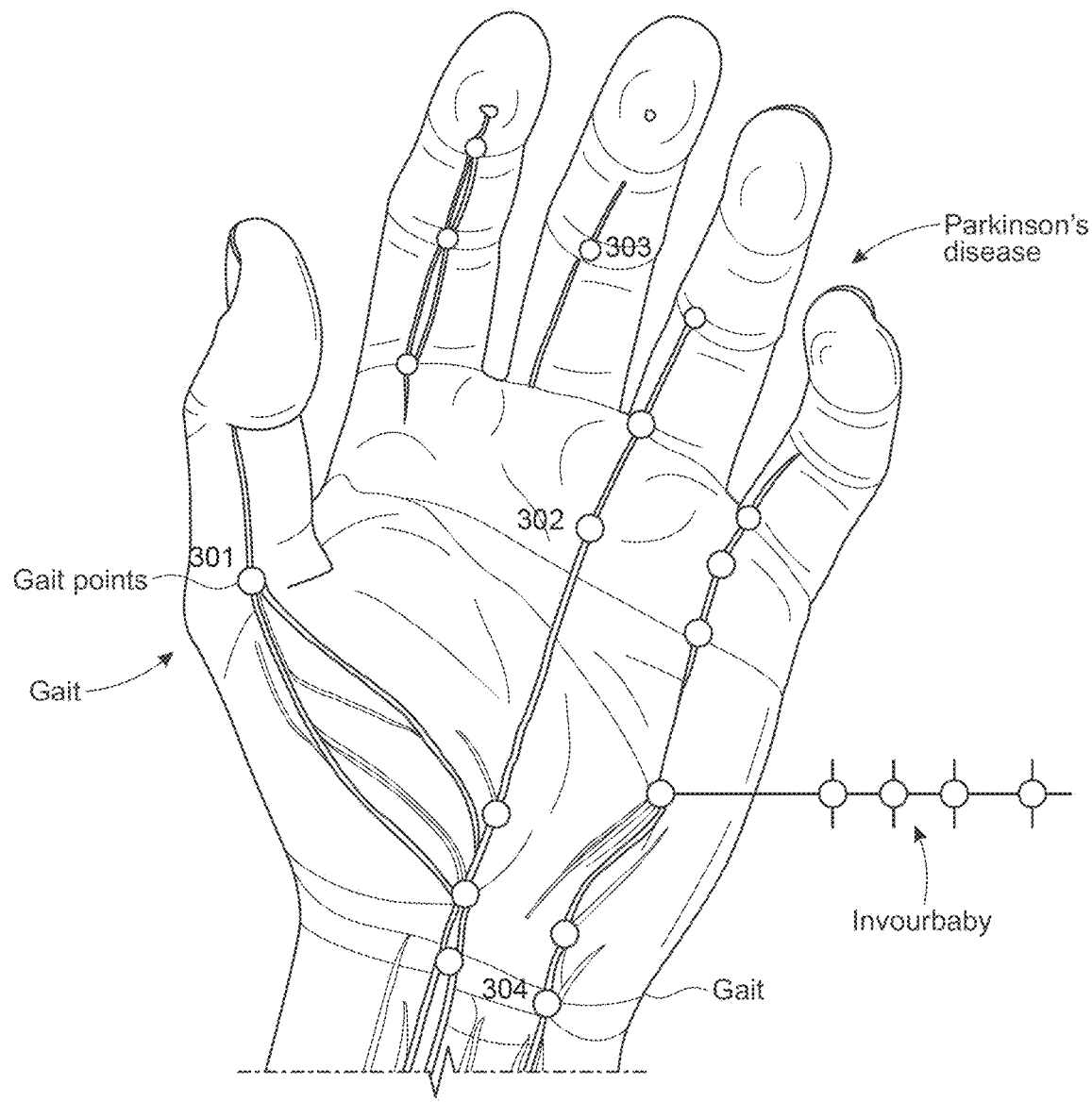
FIG. 3A illustrates an image of a hand and specific points on a hand which may be analyzed according to the tremor detection and/or analysis system or method described herein.

FIG. 3A illustrates an image of a hand and specific points on a hand which may be analyzed according to the tremor detection and/or analysis system or method described herein. FIG. 3A provides an illustration of how tremor can be extracted from video frames using characteristic gait points. In FIG. 3A, the gait points are illustrated as points 301, 302, 303 and 304 in an image of a hand 300. Another method is to extract the outline of the body part in each image frame and quantify the motion by measuring the change in the position of the outline pixels across subsequent image frames. In exemplary embodiments, using a camera or imaging device, the motion of the body part may be quantified in terms of a number of pixels or a measurement in an image. In some exemplary embodiments, in order to convert a body part motion or movement to a distance (e.g. millimeters), perspective projection techniques may be utilized in addition to other techniques. Perspective projection is described in FIGS. 8 and 9 below.

In exemplary embodiments, the tremor detection, measurement and analysis system 400 may include one or more cameras or imaging devices 420, a distance measurement device 415, a grid projection device 410, a number of wearable or attachable devices 431, 432, 445 or 446, and/or a therapy or medical computing device 425, where the therapy or medical computing device 425 may include one or more processors or controllers 460 and one or more memory devices 465 where computer-readable instructions may be stored in one or more memory devices 465. In exemplary embodiments, the wearable of attachable devices may include one or more oximetry sensors 431, one or more inertial measurement devices or sensors 445, one or more sensors with surface electromyography (sEMG sensor(s)) 432 and/or one or more pressure pad sensor(s) 446.

In exemplary embodiments, the computer-readable instructions stored in the therapy or medical computing device 425 may include a tremor analysis module 447, a video analysis module 430, a physiological analysis module 452, a posture, gait and motion analysis module 435, a muscular activation analysis module 451, a motion amplification module 441 and/or an edge detection module 442. In exemplary embodiments, the therapy or medical computing device 425 may further include a patient metrics database 440 which may be part of one or more memory devices 460 in the therapy or medical computing device 425.

In exemplary embodiments, the one or more cameras or imaging devices 420 may capture high-resolution video data (or video files) of a patient's 405 body part (e.g., a hand, arm, leg, foot, or head), while the patient body part makes various movements during exercise sessions (e.g., physical therapy sessions or other medical movement sessions). In exemplary embodiments, the one or more cameras or imaging devices 420 may be positioned to provide a clear view of a patient's body part(s). In exemplary embodiments, the one or more cameras or imaging devices 420 may transfer or communicate the video data or video files to the medical or therapy computing device(s) 425.

In exemplary embodiments, the video analysis module 430 may analyze the transferred video frames in the video data or video files to track a position of patient's body part(s) over time. In other words, a patient's one or more body parts may be analyzed by the video analysis module 430. In exemplary embodiments, the video analysis module 430 may compare a position of the body part(s) across different video frames to calculate or generate tremor amplitude measurements (e.g., distances and/or angular movements) and/or tremor frequency measurements. In other words, the tremor detection and analysis system and method may detect a presence of tremor(s), a motion or movement direction of the tremor relative to gravity, and a magnitude of a body part motion caused by the tremor. As an example, if there is a potential issue with hand tremors, the video analysis module 430 may compare positions of the hand across different video frames to detect the hand tremor and provide comparisons of the hand in different video frames (during the exercise sessions) and may generate hand tremor amplitude measurements and/or hand tremor frequency measurements. Although hand tremors are described here, the description and/or analysis of this system and method may be utilized on finger tremors, arm tremors, head tremors, leg tremors and/or foot tremors, as well as tremors on other parts of the patient's body.

In exemplary embodiments, the edge detection module 442 may enhance video recognition of tremors. In exemplary embodiments, the edge detection module 442 may apply edge detection algorithms to enhance outlines of a patient's body part in each video frame of the received video data or video files. The use of the edge detection module 442 on video frames or video data improves the accuracy of tremor measurement by clearly defining the boundaries of the body part. In exemplary embodiments, the edge detection module 440 may use various algorithms such as Canny, Sobel, or the Phase Stretch Transform (PST) algorithms. Utilizing the prior example, the edge detection module 442 may be utilized to enhance video around the patient's hand in order to more clearly detect the hand tremor and provide accuracy in measurement of the hand tremor.

In exemplary embodiments, a motion amplification module 441 may employ techniques such as Eulerian magnification to amplify subtle changes in the video frames of the received video files or video data over time. In exemplary embodiments, the use of the motion amplification module 441 may allow for improved detection and visualization of tremor movements. Utilizing the same example of a detected hand tremor, the motion amplification module 441 may amplify any hand tremor movements in the received video frames.

In exemplary embodiments, a patient metrics database 440 may receive and/or store the generated or calculated tremor amplitude measurements (e.g., distances and/or angular movements) and/or tremor frequency measurements of the patient during exercise sessions. In exemplary embodiments, the patient metrics database 440 may also store captured video communicate from the one or more cameras 420 including captured video data or video files after the captured video has been processed by the motion amplification module 441 and/or edge detection module 442.

Figure 3B:
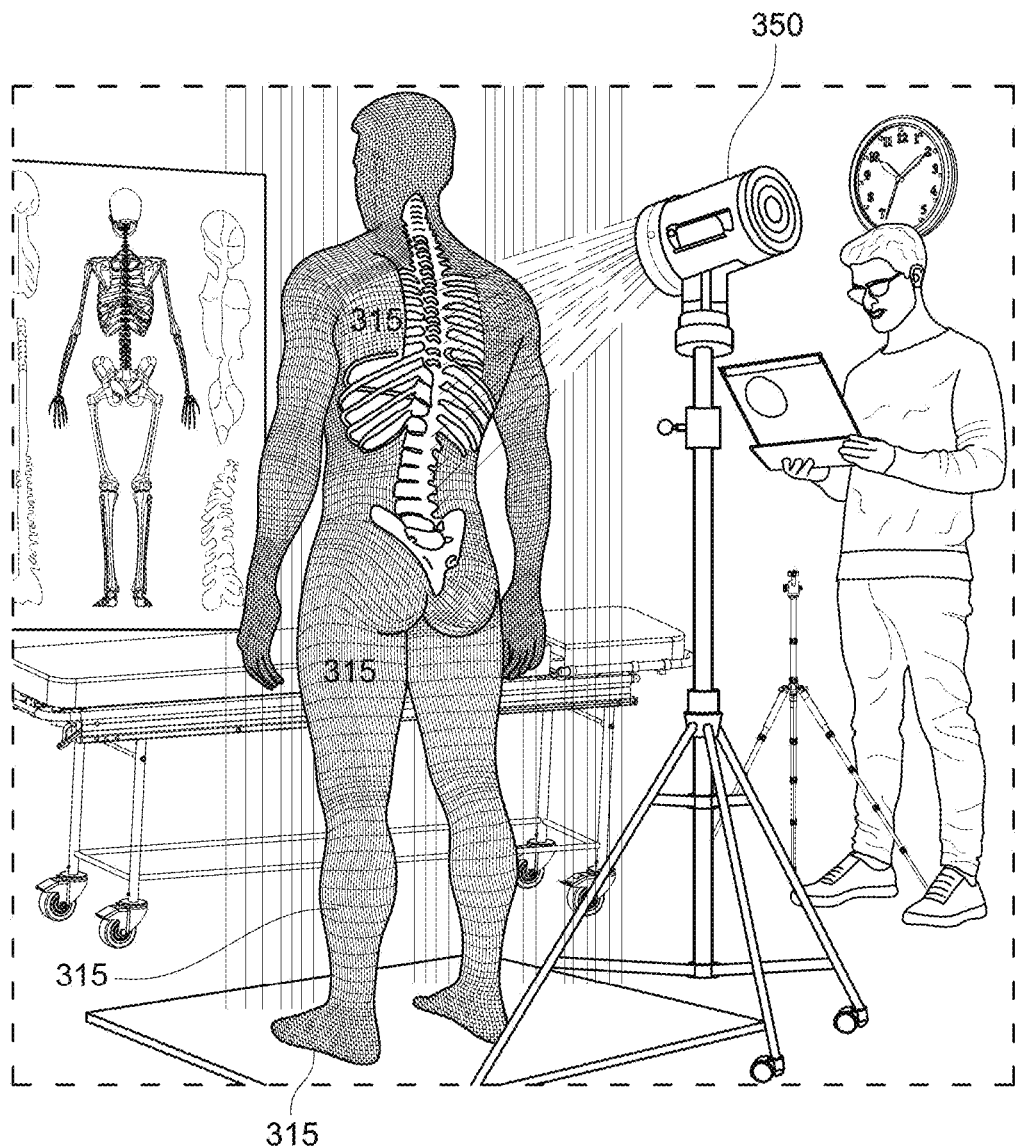
FIG. 3B illustrates a distance measuring device transmitting beams and a structured illumination transmitting beams toward a patient in order to determine postural characteristics of the patient according to exemplary embodiments.

In exemplary embodiments, a distance measuring device 415 may be utilized in a vicinity of the patient in order to determine distances between different body parts of the patient and the distance measuring device in order to determine postural characteristics of the patient. In exemplary embodiments, the distance measuring device 415 may be a light detection and ranging device (LIDAR). FIG. 3B illustrates a distance measuring device transmitting beams toward a patient as well as a structured illumination data device 410 that projects a structured pattern (e.g., a projected horizontal and vertical grid) onto the patient in order to determine postural characteristics of the patient. In exemplary embodiments, the distance measuring device 410 may project beams onto the patient 405 and may receive reflected beams back off of the patient. In these embodiments, end of flight sensors may receive the reflected beams back from the patient and may communicate the measurements to be processed in order to determine distances to the patient. In exemplary embodiments, the structured illumination device (350 in FIG. 3B) may project a structured pattern (e.g., a horizontal and vertical grid pattern 315 in FIG. 3B) onto the patient in order to provide reference areas or reference points which the system and method may utilize to assist in determining how far different parts of the body are from the distance measuring device. In other words, FIG. 3B is an illustration showing the use of a laser range finder or LiDAR, camera and structured illumination, for measuring the curvature of the spine in a patient within a physical therapy setting for diagnosis of conditions such as scoliosis or kyphosis. In exemplary embodiments, the patient curvature data or measurements may be saved in each visit allowing longitudinal assessment of patient progression over time. In the example described above, 3D patient hand curvature measurements may be generated and/or stored.

In exemplary embodiments, one or more inertial measurement device or unit(s) 445 may be worn by the patient. In exemplary embodiments, the one or more inertial measurement units (IMUs) 445 may generate three-dimensional movement data or parameters of the user. In exemplary embodiments, the one or more IMUs 445 may communicate the 3D movement unit data or parameters to the therapy or medical computing device 425. In exemplary embodiments, the communicated 3D movement data or parameters may be utilized to provide additional 3D data on tremor characteristics, which may be correlated with the video analysis results generated by video analysis module 430, edge detection module 441, and/or motion amplification module 441 (e.g., tremor amplitude measurements (e.g., distances and/or angular movements) and/or tremor frequency measurements) to enhance overall measurement accuracy of a patient's tremors. In exemplary embodiments, the 3D movement data or parameters may be stored in the patient metrics database 440.

In exemplary embodiments, the one or more wearable sensors may include surface electromyography (sEMG) technology (e.g., sEMG sensors) 432. In exemplary embodiments, the sEMG sensors 432 may be incorporated into the system to generate or calculate measure muscle activation patterns or measurements or parameters in relation to posture. The sEMG sensors 432 may provide insight into the muscular contributions to postural problems, which may be important for creating effective treatment plans. In exemplary embodiments, the sEMG sensors 432 may generate muscle activation parameters and communicate the muscle activation patterns to the therapy or medical computing device 425. In exemplary embodiments, the sEMG sensors 432 may provide biofeedback to optimize therapeutic interventions. In exemplary embodiments, the muscle activation patterns or measurements may be stored in the patient metrics database 440. In the example described above, one or more sEMG sensors may be placed on a patient's hand, and the hand muscle activation patterns or measurements may be communicated to the therapy or medical computing device for use in analysis of the patient's hand tremors.

In exemplary embodiments, the one or more wearable sensors may include one or more pressure pad sensors 446. In exemplary embodiments, the one or more pressure pad sensors 446 may be stood on by the patient or connected to the patient during prescribed exercise sessions. In exemplary embodiments, the one or more pressure pad sensors 446 may generate patient weight distribution parameters for the patients. In exemplary embodiments, the generated patient weight distribution parameters may be communicated from the one or more pressure pad sensors 446 to the computing device 425 for analysis. In exemplary embodiments, the patient weight distribution parameters may be stored in the patient metrics database 440. In exemplary embodiments, the patient weight distribution parameters may be correlated with the tremor amplitude measurements and/or tremor frequency measurements to see if the weight distribution parameters correlate or coincide with the patient tremors (e.g., occur at the same time or at similar times). In the hand tremor example, the weight distribution parameters could indicate that the patient was off balance during a time when hand tremors occurred.

In exemplary embodiments, the one or more wearable sensors may include one or more oximetry sensors 431. In exemplary embodiments, the one or more oximetry sensors 431 may be attached or connected to a patient's body 405. In exemplary embodiments, the base system or method (and the tremor detection and analysis system or method) may utilize wearable pulse and oximeter sensors 431 for real-time monitoring and collection of heart rate and blood oxygen and $CO_2$ levels during the physical therapy and rehabilitation exercises. In exemplary embodiments, the pulse and oximeter sensors 431 may generate heart rate measurements, blood oxygen levels or parameters and/or $CO_2$ levels, measurements or parameters and communicate the heart rate measurements, blood oxygen levels or parameters and/or $CO_2$ levels to the therapy or medical computing device 425 for analysis and storage. In exemplary embodiments, the physiological analysis module 452 may analyze the heart rate measurements, blood oxygen levels or parameters and/or $CO_2$ levels and generate a patient physiological assessment measurement. In exemplary embodiments, the patient physiological assessment measurement, the heart rate measurements, blood oxygen levels or parameters and/or $CO_2$ levels may be stored in the patient metric database 440. In exemplary embodiments, the patient physiological assessment measurement, the heart rate measurements, blood oxygen levels or parameters and/or $CO_2$ levels may be correlated with the tremor amplitude measurements and/or tremor frequency measurements to see if the heart rate measurements, blood oxygen levels or parameters and/or $CO_2$ level correlate or coincide with the patient tremors (e.g., occur at the same time or at similar times). In other words, when tremors are detected, the system and/or method described above may identify if the patient's heart rate or blood oxygen or $CO_2$ level changed and identify if there is a correlation. In the hand tremor example, the system or method described above may identify that a patient's blood oxygen level changes when a patient experiences hand tremors and utilize this identification in treatment of the patient.

FIGS. 5A and 5B illustrate a flowchart for a method of base operation of physical therapy system or method and the tremor detection, analysis, and/or visualization system or method according to exemplary embodiments. In step 505, the one or more cameras or imaging devices 420 may capture video data or video files of a patient's body parts during exercise routines (which may take place during a physical therapy session). In exemplary embodiments, the one or more cameras or imaging devices 420 may communicate the captured video data or video files to the physical therapy or medical computing device(s) 425.

In exemplary embodiments, in step 510, machine learning algorithms and/or computer-readable instructions may utilize a machine learning module to analyze the captured video data or video files of the patient's body parts and may also generate patient motion metrics, patient posture metrics and/or patient gait metrics for each of the patient's exercise routines. In other words, FIG. 1 illustrates postures of a patient which may be utilized for comparison to an actual patient. For example, in FIG. 1, a good posture position 105, a hollow posture position 110, a flat pelvis posture position 115, a slumped posture position 120, a military posture position 125 and a rounded shoulders posture position 130 are illustrated in FIG. 1 as potential positions of a patient. In exemplary embodiments, the patient motion metrics, patient posture metrics and/or patient gait metrics for each of the patient's exercise routines may be stored in a patient metrics database 440. In these embodiments, the machine learning algorithms may also be utilized to determine or identify postural position identification or parameters of the patient by comparing the captured images to existing images for the different posture positions identified in FIG. 1.

In exemplary embodiments, in step 515, a structured illumination device 410 may project a structure illumination pattern (e.g., a horizontal and vertical grid pattern) onto the patient to provide a plurality of reference points, reference lines or reference areas on the patient). In exemplary embodiments, a distance measuring device 415 may transmit light beams (e.g., which may be visible, infrared or ultraviolet light beams) toward the patient and the reflected beams may be captured by receivers (e.g., time of flight sensors) in order to determine a distance from the distance measuring devices 415 to the patient (or the patient's body parts). In exemplary embodiments, the therapy or medical computing device 425 may receive the measured distances may utilize the measured distances for measuring a curvature of the spine or other body part in a patient within a physical therapy setting for diagnosis of conditions (such as scoliosis or kyphosis in the case of spine curvature). In exemplary embodiments, the spine or body part curvature parameters or measurements may be saved in the patient's metrics database for each therapy session and can be utilized to track longitudinal assessment of patient progression during the therapy sessions. In exemplary embodiments, the distance may be to different body parts of a patient whereas in other embodiments, the distance may be to bone or cartilage parts of the patient's body depending on the different types of light waves used by the distance measuring device.

In exemplary embodiments, in step 520, the automated musculoskeletal and neurological analysis system may track a patient's progress during a number of physical therapy sessions by analyzing the patient's patient motion metrics, patient posture metrics and/or patient gait metrics during each of the PT sessions to determine progression or improvement over time. In some embodiments, the patient may have negative progress and this may be monitored also. In exemplary embodiments, the automated musculoskeletal and neurological analysis system 500 may generate progress parameters or assessments for each of the patients.

In exemplary embodiments, in step 525, the automated musculoskeletal and neurological analysis system may generate personalized and/or data driven therapy or medical plans to enhance patient recovery based on the analyzed data discussed above with respect to musculoskeletal and/or neurological disorders. In exemplary embodiments, the progress parameters or assessments and/or personalized or data driven therapy plans may be stored in the patient's metrics database 440.

In exemplary embodiments, in step 530, the automated musculoskeletal and neurological analysis system may also be used for tremor detection and analysis and may be referred to as a tremor detection and analysis system. In exemplary embodiment, the one or more cameras or imaging devices 420 may capture additional video data or video files of specific body parts in prescribed positions during each patient exercise routine. The body parts may be a patient head, a patient food, a patient arm, a patient elbow or other parts of the patient body, which may be subject to tremors or unexplained movements. In exemplary embodiments, the additional video data or video files may be communicated to the therapy or medical computing device 425 for analysis. Please note in some cases, the original video data or video files captured in step 505 may be utilized rather than additional video data or video files described herein in order to be more efficient. In some implementations, the additional video data or video files may also include a structured illumination pattern projected onto the patient (as described in step 515 above).

In exemplary embodiments, in step 535, a motion amplification module 441 may apply motion amplification algorithms to the additional video files or video data in order to provide clarity with respect to any tremor movements. In exemplary embodiments, the motion amplification module 441 may generate enhanced additional video files or video data (or if the original video data or video files are utilized, enhanced video data or video files with clarified tremor movements).

In exemplary embodiments, in step 540, an edge detection module 442 may apply edge detection algorithms to the additional video files or video data in order to enhance detection of tremor movement and/or boundaries of tremor movement. In exemplary embodiments, the edge detection module 442 may be applied in addition to the motion amplification algorithms or instead of the motion amplification modules. In some embodiments, if the original video data files or video data are utilized, the edge detection algorithms may be applied to those video data or video files. In exemplary embodiments, the edge detection module may generate enhanced additional video files or video data.

In exemplary embodiments, in step 545, the tremor analysis module 447 may analyze the enhanced additional video files or video data (or the enhanced video data or video files) and may generate and/or calculate tremor amplitude measurements and/or tremor frequency measurements. In exemplary embodiments, in step 550, the generated or calculated tremor amplitude measurements and/or tremor frequency measurements may be stored in the patient metrics database 440.

In exemplary embodiments, in step 550, the tremor detection and analysis module 447 may analyze the generated or calculated tremor amplitude and/or frequency measurements to diagnose whether a patient may exhibit neurological disorders such as essential tremors and/or Parkinson's disease. In exemplary embodiments, a series of the generated or calculated tremor amplitude and/or frequency measurements may be utilized to suggest a diagnosis over time. In exemplary embodiments, a neurological tremor assessment may be generated for the patient and may be stored in the patient metrics database 440. Utilizing the hand tremor example above, the tremor detection and analysis system (or the tremor detection and analysis module) may identify that there were significant hand tremors (e.g., a movement over a predetermined length) that occurred every few minutes during physical therapy exercise sessions. Based on this information, the tremor detection and analysis system (or the tremor detection and analysis module) may identify or diagnose that a patient is experiencing Parkinson's symptoms.

In exemplary embodiments, other patient data may be utilized by the automated musculoskeletal and neurological analysis system and/or the tremor detection and analysis system 400 to assist in patient health analysis and/or tremor detection and/or analysis. This information and/or data may be provided utilizing other devices (e.g., a distance measuring device 415 or a grid projection device 410) and/or may be provided by sensors or devices worn, attached to or placed in contact with a patient.

In exemplary embodiments, in step 555, sEMG sensors 432 may measure muscle activation patterns or parameters during the exercise routines of the physical therapy session and may communicate the muscle activation patterns or parameters to the therapy or medical computing device 425.

In exemplary embodiments, in step 560, the muscle activation module 451 may analyze the muscle activation patterns or parameters for abnormalities or issues and may store any abnormalities or issues along with the muscle activation patterns or parameters in the patient metrics database 440. In some implementations, the muscle activation module 451 may analyze the muscle activation pattern parameters and provide biofeedback responses to optimize therapeutic interventions based on muscular contributions to posture and movement of the patient. For example, the muscle activation module 451 may work with the tremor detection and analysis system to determine if muscle activation patterns or parameters for the body part experiencing the tremors has occurred and has any significance or relevance.

Oxygen and related sensors may also be utilized. In exemplary embodiments, in step 565, one or more oximetry sensors 431 may be attached or connected to the patient. In these embodiments, the one or more oximetry sensors 431 may capture heart rate measurements, blood oxygen levels and $CO_2$ levels, and may communicate the captured heart rate measurements, blood oxygen levels and $CO_2$ levels to the therapy or medical computing device 425. In exemplary embodiments, the therapy or medical computing device 425 may store the heart rate measurements, the blood oxygen levels, and the $CO_2$ levels in real-time in the patient metric database 440 during each exercise routine completed during physical therapy sessions. As described before, the tremor detection and analysis system or method 400 may identify whether any of these measurements change at times when tremors have been detected.

In exemplary embodiments, in step 570, the physiological analysis module 452 may analyze the received heart rate measurements, blood oxygen levels and $CO_2$ levels to determine patients physiological conditioning and may generate patient physiological conditioning parameters. In exemplary embodiments, the patient's physiological conditioning parameters may be stored in the patient metrics database 440.

Inertial measurement units may also be utilized by the automated musculoskeletal and neurological analysis system and/or the tremor detection and analysis system. In exemplary embodiments, in step 575, one or more inertial measurement units 445 may capture or record three-dimensional (3D) acceleration parameters, rotation measurements and tilt parameters during each of the exercise routines completed by the patient. In exemplary embodiments, the captured 3D acceleration parameters, rotation measurements and/or tilt parameters of the patient may be communicated to the therapy or medical computing device 425 and may be stored, in step 580, in the patient metric database 440. As described before, the tremor detection and analysis system or method 400 may identify whether any of the 3D acceleration parameters, rotation measurements and/or tilt parameters change at times when patient tremors have been detected.

In exemplary embodiments, one or more pressure pad sensors 446 may generate balance measurements of a patient standing on or connected to the pressure pad sensors 446. In embodiments, the balance measurements may be communicated to the therapy or medical computing device 425 and may be stored in the patient's metric database 440. As described before, the tremor detection and analysis system or method 400 may identify whether any of the balance measurements change at times when patient tremors have been detected.

In exemplary embodiments, in step 585, the automated musculoskeletal and neurological analysis system and/or the tremor detection and analysis system may track patient progress during the physical therapy sessions by analyzing patient recovery based on analyzed data discussed in steps 535-580 above over time. In other words, the automated musculoskeletal and neurological analysis system and/or tremor detection and analysis system may track the tremor amplitude measurements and/or tremor frequency measurements, the neurological tremor assessment, the muscle activation pattern parameters and feedback data or message, the heart rate measurements, the blood oxygen levels, and the $CO_2$ levels, the balance measurements, the patient's physiological conditioning parameters and/or the captured 3D acceleration parameters, rotation measurements and/or tilt parameters over time.

In exemplary embodiments, in step 590, the automated musculoskeletal and neurological analysis system and/or the tremor detection and analysis system may generate personalized data-driven treatment plans to enhance immediate patient recovery based on analyzed data described above in steps 505 to 585 with respect to the musculoskeletal and neurological disorders.

With respect to the system described in FIG. 4, the analysis devices described herein (e.g., the one or more imaging devices or cameras 420; the sensors 431, 432, 445, 446; the grid projection device 410, and/or the distance measuring device 415) may directly or indirectly communicate the above-identified parameters, data and/or measurements to the therapy or medical computing device 425. In other words, these analysis devices may themselves be capable of transmission (via wireless or wired communication protocols) to the therapy or medical computing device 425 or they may be communicatively coupled to other portable computing devices (e.g., laptops, tablet computing devices, network computing devices and/or wearable computing devices) that in turn then can communicate or transmit the above-identified parameters, data and/or measurements to the therapy or medical computing devices. This is also true of the systems and methods described and illustrated in FIGS. 6, 8 and 10. In addition, one or more microphones may be utilized in the system or method described herein and sound captured via the microphone may be transferred directly to a therapy or medical computing device 425 or may pass through a portable or desktop computing device before being transferred to the therapy or medical computing device. This may occur as follows. The microphone contains a diaphragm that vibrates when sound hits it. This vibration is converted into an electrical signal by the transducer in the microphone.

The analog signal from the microphone may pass through a preamplifier, usually built into the mic or sound card that boosts the signal strength. The amplified analog signal may be converted into a digital signal by the analog-to-digital converter (ADC) on the computer's sound card. The ADC may sample the analog waveform many times per second and converts the amplitudes into binary numbers. This digital data represents the original sound's waveform and this digital data may be sent to the computer's processor and software. The computer may be the portable, handheld, desktop or wearable computing device. The operating system of the computer has a sound driver that handles input from the microphone jack and recording software converts the digital data into common audio formats like WAV, MP3 etc. This creates an audio file that can be saved and edited on the computer and/or transferred to the therapy or medical computing device. Features like noise cancellation, compression, spatial filters etc. can be applied to the microphone input signal before converting to digital data. This application utilizes sound files or sound data to represent this process. The wearable sensors described herein (e.g., sEMG sensors, IMU sensors, oximetry sensors and/or balance or pressure pads) may also operate in a similar fashion where electrical signals from these sensors are converted to digital data signals and/or files that are then used and/or analyzed by the various module of the therapy or medical computing device(s) 425 (or similar computing devices in FIGS. 6, 8 and 10). As noted above, their may be intermediary computing devices between the sensor(s) and the therapy or medical computing device such as laptop, desktop, handheld, portable or wearable computing devices or controllers that receive the electrical signals (in some cases analog) and convert these signals into digital data files for processing by the software modules of the therapy and medical computing devices.

While one computing device is shown in FIG. 4, the therapy or medical computing device 425 may actually consist of multiple computing devices and/or server computing devices. The therapy or medical computing device(s) 425 may be local computing devices communicatively coupled via local area networks or personal area networks. In exemplary embodiments, the therapy or medical computing device(s) or may be cloud-based computing devices that are communicatively coupled with global communication networks (as well as other communication networks). The use of a single computing device in FIG. 4 does not limit the scope of the subject matter described herein. This is also true of the computing devices described and illustrated in the systems and methods of FIGS. 6, 8 AND 10.

Figure 7:
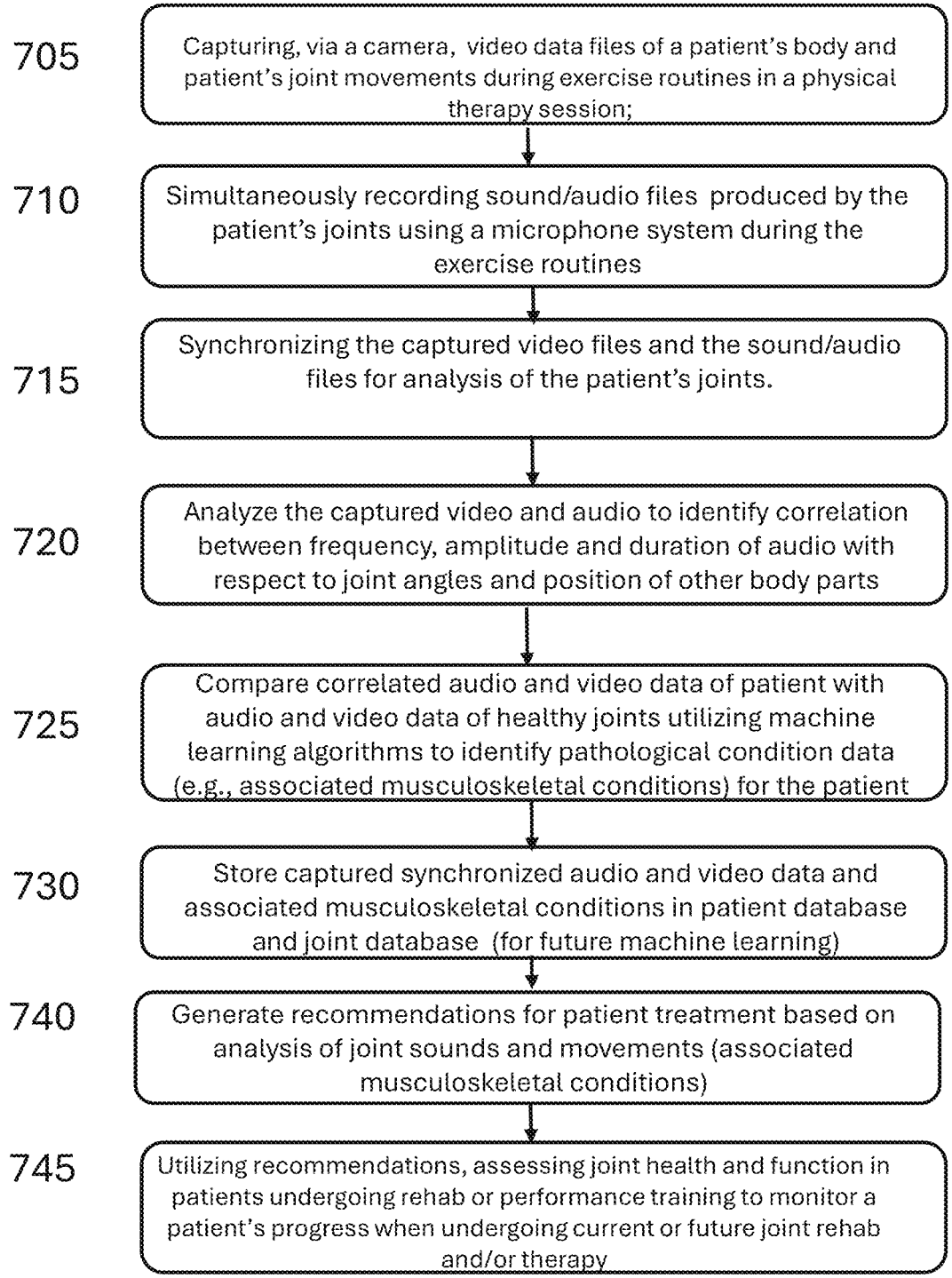
FIG. 7 illustrates a method of joint analysis according to exemplary embodiments.

FIG. 6 illustrates a block diagram of a joint analysis system according to exemplary embodiments. FIG. 7 illustrates a method of joint analysis system according to exemplary embodiments. A joint analysis described herein may assist in analyzing sounds produced during joint movement in order to provide valuable insights into musculoskeletal health of the patient. In some embodiments, the system may record the sounds made by joints during exercise and synchronize this with a video recording captured of the joint during exercise to provide a rich audiovisual dataset for diagnosis of joint health. In other words, this system may combine a simultaneous recording and quantitative analysis of the captured sound and captured video of joints during digital physical therapy (e.g., therapy exercises), and utilize this audiovisual data for diagnosing musculoskeletal health of a patient.

In embodiments, sources of joint noise may include articular noise and/or acoustic emission. Articular noise refers to joints producing sounds such as cracking, popping, or grinding when they move. These noises can occur due to gas bubble formation in synovial fluid, ligament or tendon movement over bone, and/or degenerative changes in the joint. Acoustic Emission are sounds produced by joint material undergoing deformation. Such sounds are produced by cartilage, ligaments, and/or surrounding soft tissues during movement.

In certain situations, a system may utilize microphone-based recording of sounds where high-fidelity microphones are placed around the joint of the patient to capture sounds during movement (during a therapy session). In these situations, detailed analysis of the acoustic signals produced may be performed. In some situations, spectral analysis performed on the recorded or captured sounds to identify patterns that may correlate with specific conditions, such as osteoarthritis, tendonitis, and/or cartilage degeneration.

Significant opportunity exists in creating a new system and method for diagnosis and monitoring of joint conditions via a multimodal examination consisting of both sound and quantitative video analysis. Here, sounds emanating from the joint are combined and correlated with simultaneous joint motion captured via one or more cameras or imaging devices. Subsequently, software algorithms may analyze the recorded synchronize audiovisual data to identify specific characteristics of each as well as correlation between the frequency, amplitude, and/or duration of the sound and the joint angles as well as the state of other body parts, including whole body, to provide a comprehensive analysis. Furthermore, audiovisual data from affected joints can be compared with those from healthy joints to identify abnormalities. Differences in the audiovisual signature can provide clues about the underlying pathology of the patient. Data collected from subsequent visits of the patient may be compared to assess the progression of disease or joint issue and efficacy of rehabilitation treatment.

Such a joint analysis and monitoring system and method has numerous applications. For example, in osteoarthritis, combined or synchronized audiovisual methods can help detect early changes in the joint, such as roughening of cartilage surfaces or changes in the joint space, which are indicative of osteoarthritis. In tendon and ligament injuries, abnormal sounds and motion of joints may indicate issues such as tendonitis or ligament injuries, providing insights into the condition of the soft tissues around the joint. Furthermore, changes in the sound profile and motion of the patient's joint may suggest joint instability or abnormal biomechanics, which may lead to further assessment and intervention. The new system and method of joint analysis and monitoring has numerous advantages. Because the new system and method of joint analysis and monitoring is non-invasive, the system and method can be performed in a clinical or outpatient setting including pharmacies and clinics tied to supermarkets. The system and method also may offer real-time and cost effective assessments and immediate feedback on joint function and health.

In exemplary embodiments, described herein is a new system and method for diagnosing and monitoring of a patient's joint conditions via a multimodal examination consisting of both sound analysis and quantitative video analysis. In these embodiments, sounds emanating from the joint are combined and correlated with video of simultaneous joint motion captured via a camera. In these exemplary embodiments, software algorithms may analyze the recorded audio files and captured video files (e.g., audiovisual data) to identify specific characteristics of each. In exemplary embodiments, the software described herein may identify correlation between a frequency, an amplitude, and/or a duration of the sound and the joint angles during the exercises, as well as a state or position of other body parts, including the patient's whole body, in order to provide a comprehensive evaluation of the patient.

A block diagram of the system and method of audiovisual analysis of musculoskeletal disorders 600 via simultaneous acoustic & video recording of joint motion is illustrated in FIG. 6. The system is similar to the system described in FIG. 4 for tremor detection and/or analysis with a few key differences. In FIG. 6, a plurality of microphones 605 may placed near or on the patient (and specifically the patient's joints) in order to record sounds made by a patient's joints during exercises completed during a physical training session. In exemplary embodiments, the patient may alternatively include wearable acoustic sensors, the wearable acoustic sensors attached to areas near one or more joints of the patient and configured to capture audio sounds from the one or more joints during the exercise routines completed by the patient, wherein the computer-readable instructions executed by the processors or controllers include synchronized audiovisual diagnostics to analyze the captured audio sounds of the patient's joints and the video data associated with the patient's joints during movement of the patient's joints during the exercise routines completed by the patient, to determine joint health assessment based on correlated audio sounds and video data motion patterns. In addition, the therapy or medical computing device 625 may include different modules for joint analysis, diagnosis and monitoring. In exemplary embodiments, the therapy or medical computing device 625 may include a joint information database 620 which may store joint video files, joint audio files and joint characteristics or measurements. In exemplary embodiments, the joint analysis and diagnosis system 600 may include one or more cameras or imaging devices 420, a distance measurement device 415, a grid projection device 410, a number of wearable or attachable devices and/or a therapy or medical computing device 625, where the therapy or medical computing device 625 may include one or more processors or controllers 650 and one or more memory devices 645 where computer-readable instructions may be stored in one or more memory devices 645. In exemplary embodiments, the wearable of attachable devices may include one or more oximetry sensors 431, one or more inertial measurement devices 445, one or more sensors with surface electromyography (sEMG sensor(s)) 432 and/or one or more pressure pad sensor(s) 446. In addition, the joint analysis and diagnosis system 600 may also include one or more microphones 605 placed near or close to a patient's joints. In some cases, the one or more microphones 605 may be integrated or part of other devices, such as one or more cameras and/or imaging devices 420. In other embodiments, the one or more microphones 605 may be standalone and/or a combination of integrated microphones and standalone microphones.

In exemplary embodiments, the computer-readable instructions in the therapy or medical computing device 625 may include a tremor analysis module 447, a joint information database 620, a physiological module 452, a posture, gait & motion video analysis module 435, a muscle activation analysis module 451, a 3D parameter analysis module 453, a patient metrics database 440, an audiovisual analysis module 610, and/or a machine learning joint health module 615. Many of these modules are similar to the ones described above with respect to the base system and the tremor and detection analysis module describe with respect to FIG. 4. The other modules may be described below.

In exemplary embodiments, the therapy or medical computing device 625 may include an audio-visual analysis module 610 which may synchronize the joint audio files and the joint video files as well as analyze the synchronized or combined joint audio and video files. In exemplary embodiments, the therapy of medical computing device 625 may include a machine learning joint health module 615. In exemplary embodiments, the machine learning joint health module 615 may compare the received combined joint audio visual files for the patient with existing joint audio visual files to identify if joint issues or pathologies exist and if they match existing joint audio visual files that are tied to early changes in the joint or surrounding tissues, whether tendons or ligaments are injured and/or joint instability. In exemplary embodiments, the machine learning joint health module or joint health module 615 may also store synchronized audio and visual files in the joint information database 620 that correspond to diagnosed joint issues.

FIG. 7 illustrates a flowchart for the joint analysis and monitoring method and system according to exemplary embodiments. In exemplary embodiments, in step 705, one or more cameras or imaging devices 420 may capture video data or video files of a patient's body and specifically a patient's joint movements during exercise routines in a physical therapy session. The one or more cameras or imaging devices 420 may be specifically focused on a patient's joint or joints in question.

Simultaneously, in exemplary embodiments, in step 710, the one or microphones 605 may capture or record sound files or audio sounds corresponding to the joint movements of the patients. In exemplary embodiments, the one or more cameras or recording devices 420 may be video recording devices and thus may capture sound files if close enough to the patient's joint movement. In exemplary embodiments, the one or more cameras or imaging devices 420 may communicate the captured video data or video files to the therapy or medical computing device 625. In exemplary embodiments, the one or more microphones 605 may transfer the sound or audio files to the therapy or medical computing device 625.

In exemplary embodiments, the therapy or medical computing device 625 may include computer-readable instructions including an audiovisual analysis module 610. In exemplary embodiments, the computer-readable instructions may be stored in the one or more memory devices 645 and may include the joint information database 620, the audiovisual joint analysis module 610 and synchronized audiovisual file comparison module 615 (e.g., a machine leaning joint heath module). In exemplary embodiments, in step 715, the received audio files or audio sounds may be synchronized and/or combined with the received joint video files or video data. In exemplary embodiments, the received audio files, the received video files and/or the combined or synchronized audiovisual files may be stored in the joint information database 620.

In exemplary embodiments, in step 720, the audiovisual analysis module 610 may analyze the combined or synchronized audiovisual files to identify correlations between frequency, amplitude and duration of joint sounds with respect to joint position, joint motion and/or joint angles. These correlated joint audiovisual parameters or measurements may be stored in the joint information database 620 and associated with the combined or synchronized audiovisual files.

In exemplary embodiments, in step 725, the machine learning joint health module or the joint health comparison module 615 may compare the correlated information (e.g., joint audiovisual parameters or measurements) of the patient with existing audiovisual data of healthy joints utilizing machine learning or comparison algorithms to identify joint conditions of the patient (e.g., determining if the joint is healthy or not). In exemplary embodiments, the machine learning joint health module or the joint health comparison module 615 may utilize machine learning models including unhealthy combined joint audiovisual sounds. In this way, the machine learning joint health module or joint health comparison module 615 may determine or generate a patient joint health assessment and also may determine or identify the associated joint or musculoskeletal condition associated with the patient's joint(s). In exemplary embodiments, the machine learning joint health module or joint health comparison module 615 may also generate the joint health assessment and/or associated joint or musculoskeletal condition for multiple joints or body part of the patient. In exemplary embodiments, in step 730, the synchronized audiovisual joint data or files, along with the patient joint health assessment(s) and/or joint or musculoskeletal condition(s) may be stored in the joint information database 620.

In exemplary embodiments, in step 740, the joint analysis and monitoring system may generate recommendations for patient treatment based on the analysis of the synchronized joint audiovisual data and movements, the patient joint health assessment(s) and/or the patient joint/musculoskeletal condition(s). In exemplary embodiments, in step 745, the joint analysis and monitoring system or method may then monitor a patient's progress with respect to joint health and function when undergoing current or future joint rehab and/or therapy. In exemplary embodiments, the joint analysis and monitoring system 600 may be utilized on any of a patient's joints or multiple patient joints. This may include, but not be limited to a patient's neck, shoulder, elbow, wrist, fingers, toes, ankles, knees, hips and/or other body parts.

Figure 8:
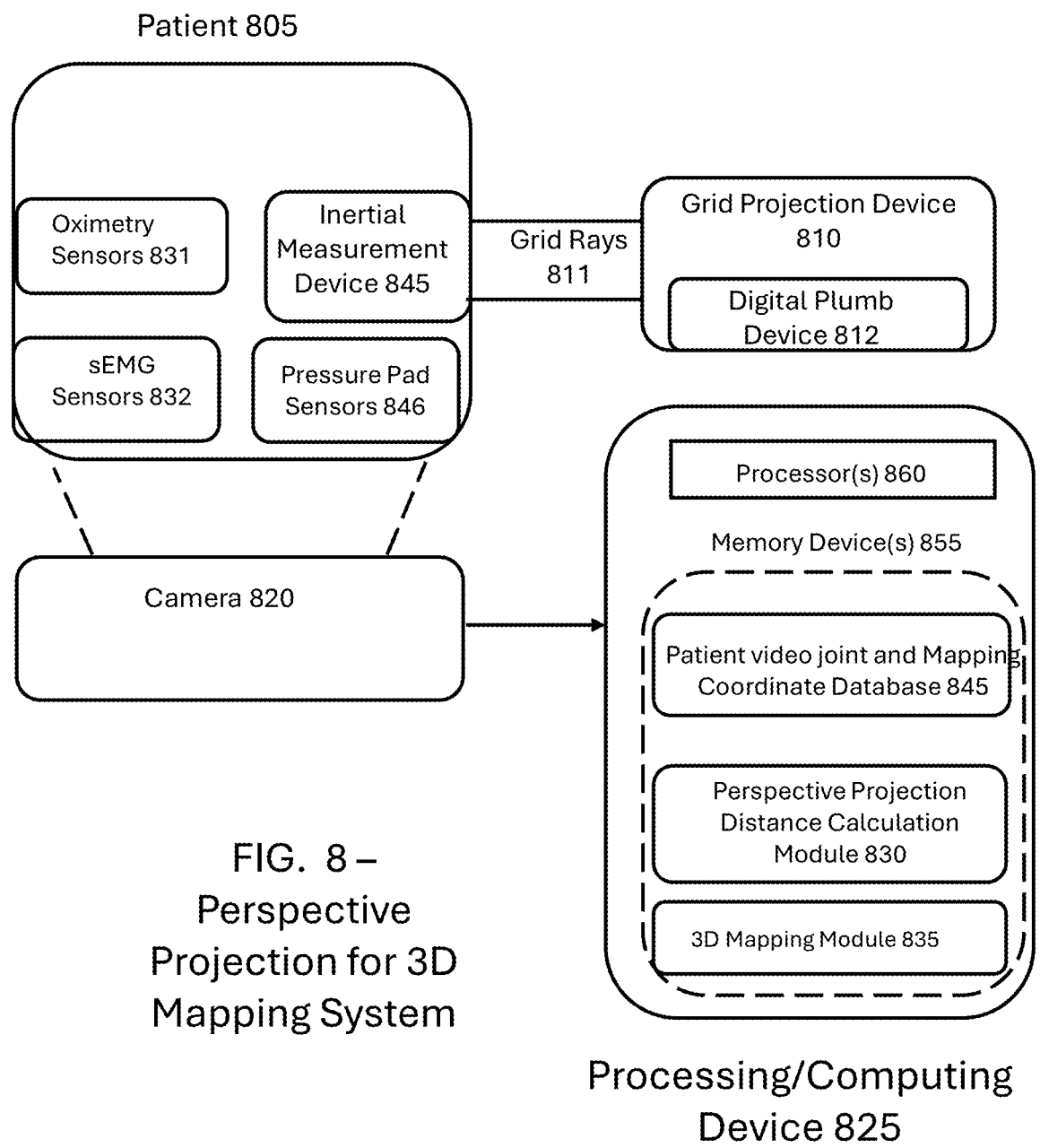
FIG. 8 illustrates a block diagram of a perspective projection for three-dimensional (3D) mapping system according to exemplary embodiments.

Described herein is a system and method for generating three-dimensional maps of a patient. FIG. 8 illustrates a block diagram of a perspective projection for three-dimensional (3D) mapping system according to exemplary embodiments. Perspective projection is a fundamental concept in optical imaging and computer vision that describes how three-dimensional objects are represented in two dimensions (such as on a camera sensor or screen). In exemplary embodiments, the perspective projection technique or algorithm may mimic a way human eyes may perceive the world, and thus may create images that maintain a spatial relationship of objects (and between objects) and/or also depth of objects.

In exemplary embodiments, combining perspective projection techniques or algorithms with structured illumination techniques may be a powerful approach for obtaining detailed three-dimensional (3D) maps of objects or people. In exemplary embodiments, a system or method that leverages the strengths of both perspective projection techniques and/or structure illumination techniques may enhance an accuracy and richness of the captured data and the generated 3D map coordinates or associated images.

Structured illumination involves projecting a known pattern (such as lines, grids, points or dots) onto a surface of an object or a person. In these embodiments, the structured pattern may help create distinct features on an object's surface that can be easily tracked and analyzed. In exemplary embodiments, the use of structured patterns may allow for better depth perception and surface detail capture, especially in cases where the object's or person's texture is minimal or difficult to discern. In perspective projection, one or more camera or imaging devices capture an image file or video files (video data) of the object or person from a specific viewpoint, and projects the 3D coordinates of points on the object into 2D image coordinates. In exemplary embodiments, by using a calibrated camera or imaging device, the spatial relationships between points in 3D space may be maintained, allowing for accurate depth mapping. In exemplary embodiments, an integration of structured illumination algorithms with perspective projection algorithms may provide a robust framework for creating accurate and detailed 3D maps of objects or people. This combined structured illumination and perspective projection methodology enhances both a depth and a quality of the captured data, making the data a valuable tool across various fields, from industrial applications to medical imaging and beyond. For example, the combined structured illumination and perspective projection methodology may have uses in a) Medical Imaging: used in techniques like optical coherence tomography (OCT) to create detailed 3D images of biological tissues; b) Industrial Inspection: Structured illumination can help in quality control by mapping the surface of manufactured parts to detect defects or deviations from design specifications; and/or c) Robotics: Enables robots to perceive and interact with their environment by providing accurate 3D maps for navigation and manipulation.

FIG. 8 illustrates a three-dimensional mapping system utilizing structured illumination and perspective projection techniques according to exemplary embodiments. FIG. 8 includes the same sensors included in FIGS. 4 and 6 as well as a therapy or medical computing device 825 which is similar to the therapy or medical computing device 425 in FIGS. 4 and 6. In exemplary embodiments, the three-dimensional mapping system may include a grid projection or structured illumination device 810. In exemplary embodiments, the structured illumination device 810 may project a uniform pattern (e.g., horizontal or vertical lines) onto a patient, person or object (which may be referred to as grid rays 811. This also applies to the grid projection device or structured illumination devices (410 and 610 in FIGS. 4 and 6). In exemplary embodiments, the background may include a grid pattern with evenly spaced lines that serve as a reference for analyzing body part movements. In these embodiments, this projected grid pattern may help in quantifying positions or movements by providing a stable, consistent frame of reference. In exemplary embodiments, one or more digital plumb devices 812 may also assist in making sure that the structured illumination device is projecting grid rays 811 that are referenced to a ground plane or another vertical or horizontal axis. In other words, the one or more digital plumb devices 814 or 412 (for FIG. 4) may make sure the projected grid or illuminated pattern is level with respect to a reference line and/or plane. In exemplary embodiments, this keeps the illuminated pattern straight and/or accurate. In exemplary embodiments, the projected grid pattern may be provided by structured illumination of a laser pattern onto the patient positioned against a uniform and flat backdrop. In some embodiments, the laser pattern may be leveled using an inertial pendulum mechanism 812, such as a digital plumb device. In exemplary embodiments, the one or more cameras or imaging device 820 may capture video data or video files of the patient with a patterned grid projected thereon by a grid projection device 810. In exemplary embodiments, the captured video data or video files may be communicated to the therapy or medical computing device 825 for analysis and processing. In exemplary embodiments, the captured video data or video files may be stored in a patient video database 845. In exemplary embodiments, the patient video database 845 may be located in one or more memory devices of the therapy or medical computing device 825. In exemplary embodiments, the captured video data or video files include the structured illumination pattern.

In exemplary embodiments, the therapy or medical computing device 825 include computer-readable software or instructions which are executable by one or more processors 860. In exemplary embodiments, the computer-readable software or instructions may be stored in one or more memory devices 855 of the therapy or medical computing device 825. In exemplary embodiments, the therapy or medical computing device 825 may include a perspective projection distance calculation module 830, the 3D mapping module 835 and/or also the patient video joint and mapping coordinate database 845. In exemplary embodiments, the perspective projection distance calculation module 830 may calculate distances to the patient or object in order to allow three-dimensional mapping. In exemplary embodiments, the three-dimensional (3D) mapping module 835 may generate three-dimensional maps of the patient for use in providing precise diagnostics and continuous monitoring of the patient.

A software code library for computational imaging includes ready to use algorithms for measuring the distance (i.e. range) to the object if some of the following variables are known: the focal length of the camera; the real-world size of the patient or object; and/or the size of the patient or object in the captured image (which may be in terms of pixels). An example calculation module may include the following algorithm: import: #Assuming you have calibrated your camera and know the focal length (focal_length=500); #pixels; #Known real-world size of the object (e.g., in cm) (real_width=10); #Detect the object in the image and measure its width in pixels. (image_width=50) and calculated the distance using the equation: distance=(real_width*focal_length)/image_width. In some implementations, a RealWorldDistanceCalculator class leverages camera parameters like focal length and distortion coefficients to model real-world distances accurately. It initializes a camera matrix essential for correcting radial and tangential distortions previously discussed.

In exemplary embodiments, a calculate_distance method may computes the real-world distance between two pixel points by employing the cv2.undistortPoints function. This function undistorts the input pixel coordinates, allowing for accurate measurements by mitigating distortion effects. For example, the functional may be as follows:

undistorted_points=cv2.undistort Points(points,camera_matrix,dist_coeffs,P=camera_matrix)

In some implementations, the final real-world distance may be calculated using the formula:

$$real\_world\_distance = \frac{pixel\_distance \times distance\_to\_wall}{focal\_length\_pixels}$$

where the pixel distance is derived from the Euclidean distance between the undistorted points, ensuring high precision in the measurement process.

Figure 9:
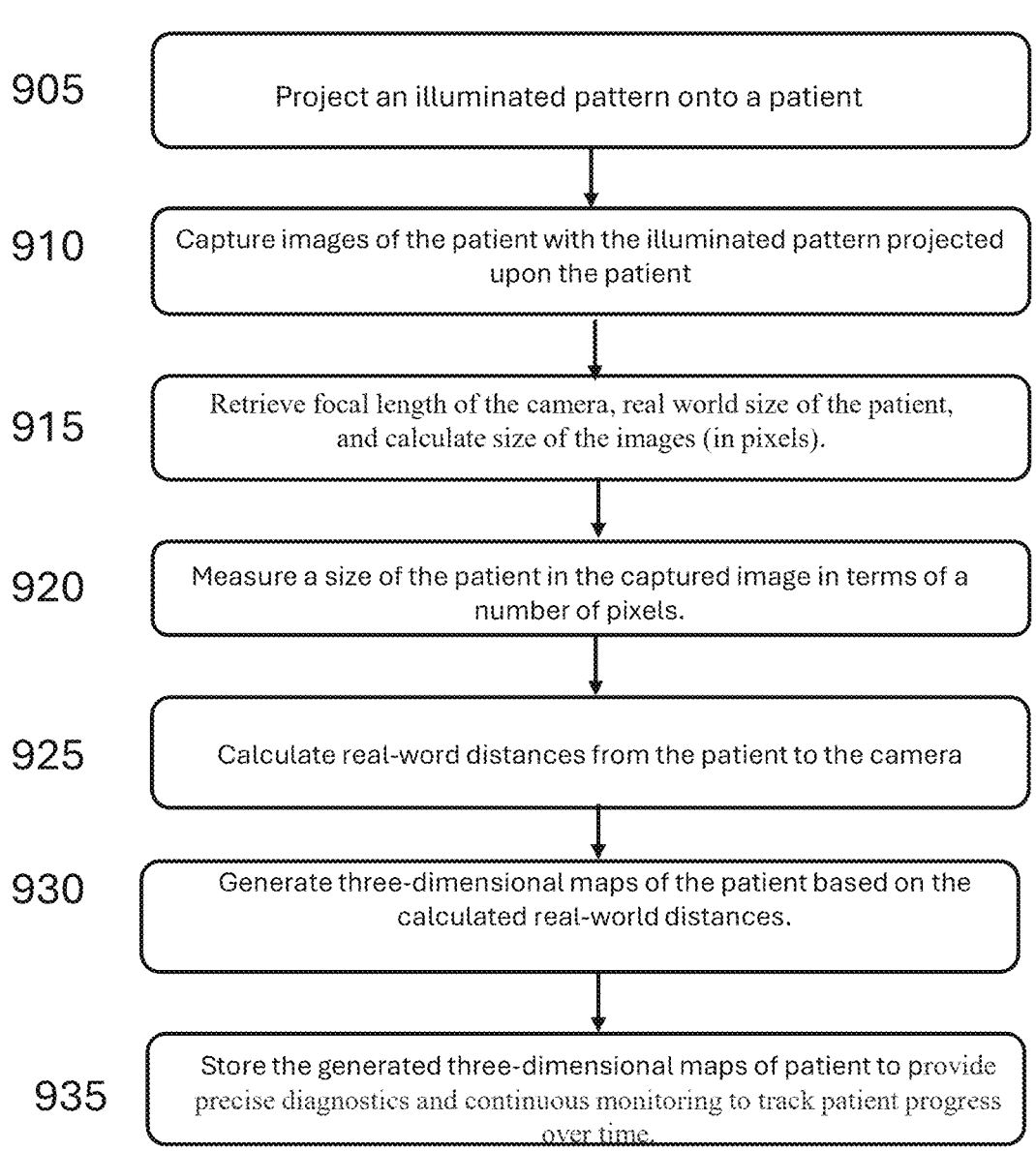
FIG. 9 illustrates a flowchart of a three-dimensional mapping system or method using structured illumination and perspective projection techniques according to exemplary embodiments.

FIG. 9 illustrates a flowchart of a three-dimensional mapping system or method using structured illumination and perspective projection techniques according to exemplary embodiments. In exemplary embodiments, in step 905, the structured illumination projection device may project an illuminated pattern onto a patient. In some implementations, this may create a patterned grid on the patient. In some implementations, the projected grid may be made utilizing a laser device or a laser leveling device. In exemplary embodiments, the illuminated pattern may be a plurality of horizontal and vertical reference lines or reference points.

In exemplary embodiments, in step 910, one or more cameras or imaging devices 820 may capture image data or image files (e.g., could be video files) of the patient with the illuminated pattern. By having the illuminated pattern, there will now be reference points or reference areas on the patient (e.g., the reference points may be the points where the illuminated grid intersects horizontally and vertically or the reference areas may be the areas created or formed by the illuminated pattern. In exemplary embodiments, the reference areas may be formed by the plurality of reference lines or the reference areas. These plurality of reference areas, the plurality of reference points or the plurality of reference lines can be utilized as the points are areas, points or lines that the distances are calculated from or to. In exemplary embodiments, the captured image data or image files including the projected illumination pattern may be communicated to the therapy or medical computing device 825.

In exemplary embodiments, in step 915, the one or more cameras 820 (or imaging devices) may have a focal length which may be provided to the therapy or medical computing device 825 along with a real world size of the patient (e.g., a width or length of the patient). In exemplary embodiments, in step 920, the system or method described here may measure a size of the patent in the captured image in terms of a number of pixels. In these embodiments, the perspective projection distance calculation module 830 may determine a size of the patient based at least in part on the plurality of reference points, the plurality of reference lines or the plurality of reference areas by detecting specific points or areas in the captured image files or video files. Once the patient reference points or reference areas are detected, in step 925, the perspective projection distance calculation module 830 may calculate a distance to the patient. In some embodiments, the plurality of reference lines, the plurality of reference points or the plurality of patient reference areas may represent where the patient is located with respect to the one or more cameras. In exemplary embodiments, the perspective projection distance calculation module 830 may determine these calculated distances for all of the patient's body if the one or more cameras or imaging devices capture images of all different views of the patient.

In exemplary embodiments, in step 930, the three-dimensional (3D) mapping module may generate 3D mapping coordinates for the patient, based at least in part for the calculated distances, for the patient reference points or patient reference areas. In exemplary embodiments, in step 935, the 3D mapping module 835 may store the mapping coordinates in the patient mapping database 845. The maps that are created by the mapping coordinates may be utilized to provide precise diagnosis and continuous monitoring to track patient progress over time.

FIG. 10 illustrates a block diagram of a balance detection, analysis, and diagnosis system or method according to exemplary embodiments. The balance detection, analysis and diagnosis system or method 1000 may assist patients with diabetes-induced and/or chemotherapy-induced neuropathy.

Diabetes induced and chemotherapy-induced neuropathy are two common conditions that can significantly affect a person's sensory and motor functions, increasing the risk of falls, especially among patients and older adults. Diabetic neuropathy is a complication of diabetes resulting from prolonged high blood sugar levels, which damage the nerves throughout the body. It affects the peripheral nerves, which can lead to loss of sensation, pain, and weakness, primarily in the legs and feet. Chemotherapy-induced peripheral neuropathy (CIPN) is a common side effect of cancer treatments involving neurotoxic agents. CIPN can lead to similar symptoms as diabetic neuropathy. Symptoms of neuropathy include numbness and tingling in the patient's hands and feet, which can affect the patient's ability to sense their environment. Muscle weakness can occur, particularly in the lower limbs, impacting the patient's mobility and balance. Neuropath may also cause problems with fine motor skills in the hands can affect tasks that require dexterity, such as gripping or holding objects.

Both diabetes-induced and chemotherapy-induced neuropathy contribute to a heightened risk of falls for several reasons: 1) Loss of Sensation-Patients may not be able to feel their feet or the ground, leading to difficulty in adjusting their balance. This lack of sensory feedback can result in missteps and falls of the patient; 2) Weakness in the lower extremities can impair the ability to stand up, walk, or navigate stairs, significantly increasing the likelihood of falls of the patient; 3) Visual Impairments-Neuropathy can sometimes be associated with visual disturbances, which further complicates spatial awareness and balance of the patient; and 4) Delayed Reaction Times-Neuropathy can slow reaction times of the patient, making it difficult for patients to respond quickly to changes in their environment, such as stumbling or losing balance. Balance Screening and Training: In exemplary embodiments, physical therapy and balance training exercises can improve stability and strength, helping to mitigate the risk of falls. In exemplary embodiments, both the balance screening and training may be facilitated with an intelligent camera and associated balance detection, analysis, and diagnosis system or method to measure, quantify and store quantitative gait and balance data on patients.

In exemplary embodiments, the digital physical therapy system and method 1000 described herein offers a multifaceted approach to help treat patients suffering from neuropathy-induced loss of balance. By providing comprehensive assessments, targeted rehabilitation exercises, and continuous monitoring, the digital physical therapy system and method 1000 minimizes the risk of falls and enhances the overall safety and quality of life for these neuropathy patients.

FIG. 10 is a block diagram illustrating a balance analysis and diagnosis system and method according to exemplary embodiments. The balance analysis and diagnosis system's 1000 and method's ability to perform detailed posture and gait analysis and allow healthcare professionals to assess the specific ways neuropathy affects a patient's movement. In exemplary embodiments, by capturing the patient's movements and analyzing them in real time, clinicians and therapy practitioners may identify balance deficiencies, gait abnormalities, and the severity of neuropathy impacts. In exemplary embodiments, the system and method may allow patients to report pain levels and locations during exercises. This pain reporting feature helps tailor therapy to minimize discomfort while focusing on balance and strength training. In addition, this pain reporting and mapping allows visualizing areas of pain in conjunction with patient movement data, clinicians can adjust therapeutic exercises to avoid exacerbating pain, ensuring a more effective rehabilitation process. Based on the data collected, the balance analysis and diagnosis system and method 1000 can generate personalized exercise regimens that focus on improving balance and coordination.

In the balance analysis and diagnosis system and method adding a structured illumination device 1010 and feature allows quantification of balance relative to gravity. The structured illumination device 1010 feature also helps patients visualize their movements and positions enhancing their awareness and control over their balance during exercises. The balance analysis and diagnosis system and method may also include patient wearable sensors, such as electromyography (sEMG) sensors, which may help track muscle activation patterns, and provide biofeedback that encourages proper movement techniques and helps improve balance during physical therapy exercise routines. Further, the balance analysis and diagnosis system and method 1000 may provide real-time feedback to patients during exercises, helping them understand their movements better and make necessary adjustments. In exemplary embodiments, the balance analysis and diagnosis system and method may include one or more microphones 1012. In exemplary embodiments, the one or more microphones 1012 may capture sounds or audio files from the patient reporting conditions during physical therapy, which could include pain location parameters and/or pain intensity measurements. In exemplary embodiments, the therapy or medical computing device(s) 1045 may be similar to the therapy or medical computing devices in FIGS. 4, 6 and 8. In addition, the therapy or medical computing device(s) 1045 may include one or more processors 1085 and/or one or more memory devices 1090. Computer-readable instructions may be stored in the one or more memory devices. The computer-readable instructions may include the software modules described previously in FIGS. 4, 6 and 8. These modules may include tremor analysis module 1050, the physiological analysis module 1055, the posture, gait, nd motion analysis module 1060, and/or the patients metric database 1070. In addition, the computer-readable instructions (stored in the one or more memory devices 1090 may be executable by one or more processors 1085) may also include the balance analysis module 1075, the pain analysis module 1065 and/or the patient therapy plan or module 1080.

In exemplary embodiments, the balance analysis and diagnosis system and method 1000 may include progressive training. Progressive training allows the system and method, as patients improve, to adapt exercises to gradually increase difficulty, ensuring continued progress and challenge without overwhelming the patient during physical therapy. In exemplary embodiments, the ability to store and analyze data over time in the balance analysis and diagnosis system and method allows clinicians to track the patient's progress and make informed decisions about ongoing treatment strategies. Further, the balance analysis and diagnosis system and method 1000 may analyze changes in gait and balance over time, so the system and method can help identify increasing fall risk and prompt timely interventions. In exemplary embodiments, if the patient cannot frequently visit a clinic, the system's telehealth capabilities allow for remote monitoring and therapy sessions, ensuring continuous care and adjustment to their rehabilitation program.

Figure 11A:
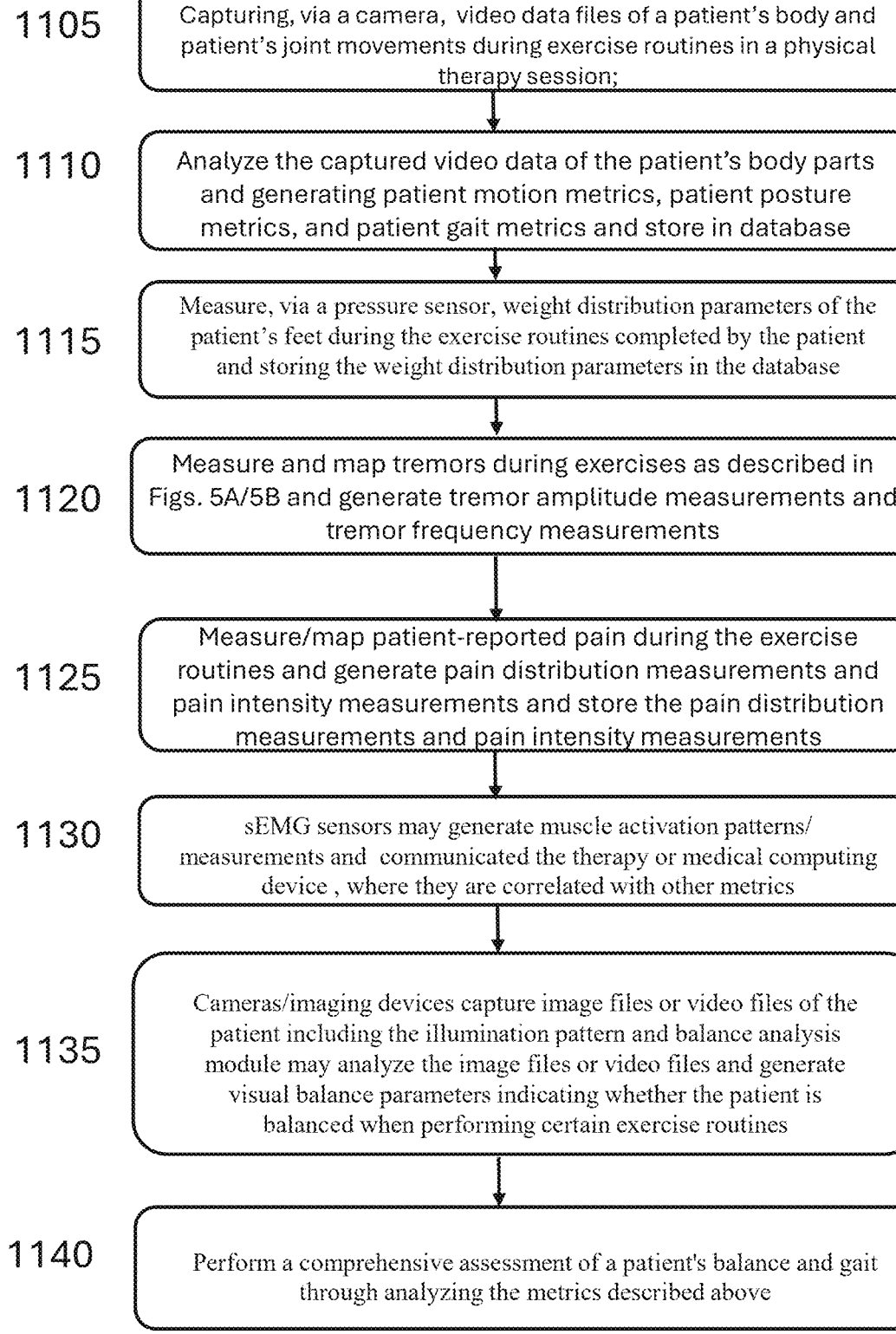
FIG. 11A illustrates a flowchart of a method and system for balance detection, analysis, and diagnosis according to exemplary embodiments.

FIG. 11 illustrates a flowchart of a method and system for balance detection, analysis, and diagnosis according to exemplary embodiments. In exemplary embodiments, in step 1105, the one or more cameras or imaging devices 1010 may capture video data or video files of a patient's body and patient's joint movements during exercise routines in a physical therapy session. In exemplary embodiments, the captured video data or video files may be communicated to the therapy or medical computing device(s) 1045.

In exemplary embodiments, in step 1110, the posture, gait and motion video analysis module may analyze the captured video data or video files of the patient's body parts and generates patient motion metrics or measurements, patient posture metrics or measurements, and/or patient gait metrics. In exemplary embodiments, the patient motion metrics or measurements, patient posture metrics or measurements and/or patient gait metrics may be stored in the patient's metrics database 1070.

In exemplary embodiments, in step 1115, the one or more pressure pad sensors 1030 may measure and generate weight distribution parameters of the patient's feet during the exercise routines completed by the patient during a physical therapy session. In exemplary embodiments, the weight distribution parameters are communicated to the therapy or medical computing device 1045. In exemplary embodiments, the weight distribution parameters are stored in the patient's metrics database 1070. In exemplary embodiments, for example, the weight distribution parameters may indicate the patient is perfectly balanced (even weight distribution parameters); is right- or left-leaning (e.g., off balance horizontally to the left or right), is forward- or rear-leaning (e.g., off balance because the patient is leaning forward—e.g., on their toes or leaning backward—e.g., on their heels). In addition, the weight distribution parameters may indicate the patient is too forward vertically (meaning the patient's top part of the body is in front of the bottom part of the patient's body) or too rear vertically (meaning the patient's bottom part of the body is in front of the top part of the body). In exemplary embodiments, different weight distribution parameter values may represent these different balance profiles.

In exemplary embodiments, in step 1120, the tremor analysis module 1050 may analyze the captured video data or video files (or additional video data or additional video files) as described above in FIGS. 4, 5A and 5B, and may generate tremor amplitude measurements and tremor frequency measurements. In exemplary embodiments, the tremor amplitude measurements and tremor frequency measurements may be stored in the patient metrics database 1070.

In exemplary embodiments, in step 1125, the patient may communicate pain location and intensity information (e.g., one or more microphones 1010 may capture patient's verbal pain information or a computing device may receive as input a patient's pain information). In exemplary embodiments, the pain location measurements and/or pain intensity parameters may be communicated to the therapy or medical computing device 1045. In exemplary embodiments, a pain analysis module 1065 may analyze the pain location measurements and pain intensity parameters and map these onto the patient's body or body part. In exemplary embodiments, the pain location measurements, the pain map and the pain intensity parameters may be stored in the patient metric database 1070.

In exemplary embodiments, in step 1130, the one or more sEMG sensors May 1030 may generate muscle activation patterns or measurements and the muscle activation patterns or measurements may be communicated the therapy or medical computing device 1045. In exemplary embodiments, the muscle activation analysis module 1062 may analyze the muscle activation patterns or measurements and correlate the muscle activation patterns or measurements with other patient metrics. In exemplary embodiments, the muscle activation patterns or measurements along with the correlation parameters may be stored in the patient metric database 1070.

In exemplary embodiments, the structured illumination device 1010 may generate an illumination pattern onto the patient. In exemplary embodiments, in step 1135, the one or more cameras or imaging devices 1040 may capture image files or video files of the patient including the illumination pattern (e.g., such as a horizontal and vertical grid pattern projected onto the patient). In exemplary embodiments, the image files or video files including the projection illumination pattern may be communicated to the therapy or medical computing device 1045. In exemplary embodiments, the balance analysis module 1075 may analyze the image files or video files and generate visual balance parameters indicating whether the patient is balanced when performing certain exercise routines. In other words, this structured illumination feature allows quantification of patient balance relative to gravity. The use of structured illumination also helps patients visualize their movements and positions enhancing their awareness and control over their balance during exercises.

In exemplary embodiments, in step 1140, the balance analysis module 1070 may perform a comprehensive assessment of a patient's balance and gait through analyzing the metrics described above and may generate a patient's balance parameters and balance assessment and may store the patient's balance parameters and balance assessment in the patient metrics database.

In exemplary embodiments, in step 1145, the therapy plan module 1080 may generate or create personalized targeted rehabilitation exercises or exercise adjustments to the patient's current therapy exercise program to improve balance, coordination, and strength based on metrics described above along with the patient's balance parameters and balance assessment.

In exemplary embodiments, in step 1150, the therapy plan module 1080 may provide real-time feedback and biofeedback to the patient via a patient's computing device during the physical therapy session (or before or after the physical therapy session) to guide the patient in making necessary adjustments for balance improvement.

In exemplary embodiments, in step 1155, the therapy plan module 1080 may measure a patient outcome with respect to the various measurements and parameters discussed above based on the adjustments to the physical therapy sessions described above and may generate therapy session outcome parameters.

Figure 12:
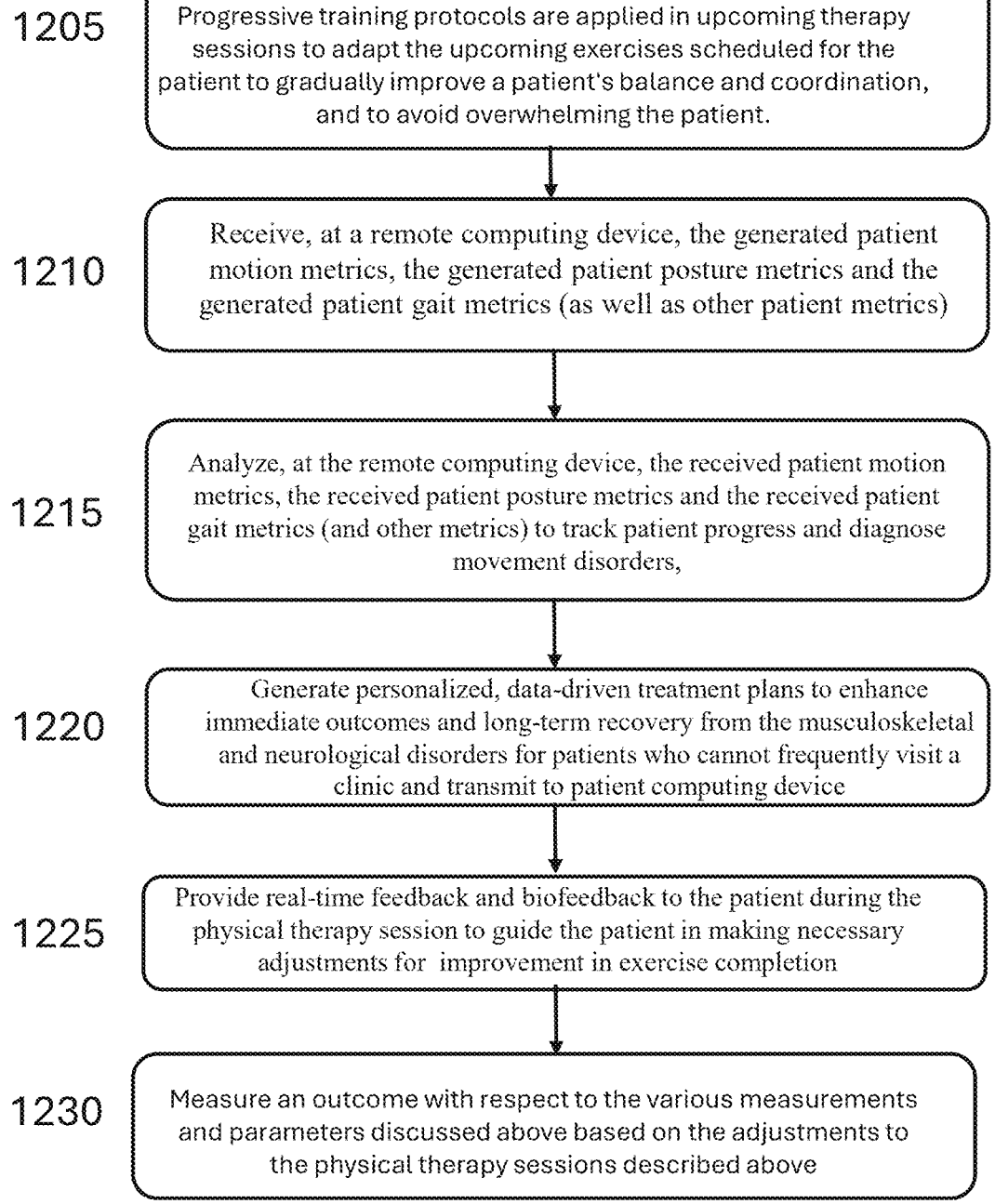
FIG. 12 illustrates a flowchart for how a system and method for automated diagnosis of musculoskeletal and neurological disorders may be utilized in accordance with some embodiments.

FIG. 12 illustrates a flowchart for how a system and method for automated diagnosis of musculoskeletal and neurological disorders may be utilized according to exemplary embodiments. In exemplary embodiments, in step 1205, the system and method described in FIGS. 4-11 may progressively apply training protocols in upcoming therapy sessions to adapt upcoming exercise routines scheduled for the patient to gradually improve a patient's balance and coordination over time, while at a same time avoid overwhelming the patient. The system and methods described in FIGS. 4-11 may be utilized by medical or therapy professionals who are remote from the patients (e.g., teletherapy or telehealth). In exemplary embodiments, in step 1210, a remote computing device may receive generated patient motion metrics, the generated patient posture metrics and the generated patient gait metrics (as well as other patient metrics), as described above with respect to FIGS. 4-11. In these embodiments, in step 1215, the therapist or medical practitioner along with the system and method for automated diagnosis of musculoskeletal and neurological disorders may analyze, at the remote computing device, the received patient motion metrics, the received patient posture metrics and the received patient gait metrics (and other metrics) to track patient progress and diagnose movement disorders.

In exemplary embodiments, in step 1220, the system and method for automated diagnosis of musculoskeletal and neurological disorders may generate personalized, data-driven treatment plans based on the analyzing of the received patient metrics described above to enhance immediate outcomes and long-term recovery from the musculoskeletal and neurological disorders for patients who cannot frequently visit a clinic. In these embodiments, the remote computing device may transmit these personalized data-driven treatment plans to patient computing devices and/or the therapy or medical computing device In exemplary embodiments, in step 1225, the system and method for automated diagnosis of musculoskeletal and neurological disorders may provide real-time feedback and biofeedback to the patient (via the therapy or medical computing device or a patient's computing device) during a physical therapy session to guide the patient in making necessary adjustments for improvement in exercise completion. The real-time feedback and biofeedback may be based on the analyzation and recommendations completed by the system and methods described in FIGS. 4-11. In exemplary embodiments, in step 1230, system and method for automated diagnosis of musculoskeletal and neurological disorders may measure an outcome with respect to the various measurements and parameters collected and discussed above in FIGS. 4-11 based on the adjustments to the physical therapy sessions described above in step 1225, and may store the outcome of the recommendations and feedback in the therapy or medical computing devices and/or databases described in FIGS. 4-11.

A digital physical therapy system for diagnosing, treating, and rehabilitating patients with musculoskeletal and neurological disorders includes a plurality of cameras configured to capture video data of a patient's body parts during exercise routines and configured to capture additional video data of specific patient's body parts in prescribed positions during each exercise routine; one or more processors or controllers; one or more memory devices; and computer-readable instructions, including machine learning algorithms and stored in the one or more memory devices, and executable by the one or more processors or controllers to, the computer-readable instructions to: analyze the captured video data of the patient's body parts and to generate patient motion metrics, patient posture metrics, and patient gait metrics for each exercise routine completed by the patient based on the analyzed video data; store, in a database, the generated patient motion metrics, the patient posture metrics and the patient gait metrics for each of the completed exercise routines, wherein the generated patient motion metrics, the generated patient posture metrics and the generated patient gait metrics are used to track patient progress during physical therapy sessions, diagnose movement disorders, and provide personalized, data-driven treatment plans to enhance immediate outcomes and long-term recovery with respect to the musculoskeletal and neurological disorders; apply motion amplification algorithms to enhance the additional video data to provide clarity of tremor movements; apply edge detection to enhance tremor movement boundaries and detection; generate tremor amplitude measurements and tremor frequency measurements based on the motion amplification and edge detection algorithms; and store, in the database, the generated tremor amplitude measurements and tremor frequency measurements, wherein the generated tremor amplitude measurements and tremor frequency measurements are analyzed for diagnosis and monitoring of disorders such as Parkinson's disease and Essential Tremors.

In exemplary embodiments, the digital physical therapy system includes wearable surface electromyography (sEMG) sensors, the sEMG sensors attached to the patient and configured to measure muscle activation pattern parameters, and store the muscle activation pattern parameters in the database, wherein the muscle activation pattern parameters provide biofeedback to optimize therapeutic interventions based on muscular contributions to posture and movement of the patient. In exemplary embodiments, the digital physical therapy system includes wearable oximetry sensors, the wearable oximetry sensors attached to the patient, and configured to capture heart rate measurements, blood oxygen levels and $CO_2$ levels, and to store the heart rate measurements, the blood oxygen levels, and the $CO_2$ levels in real-time during each exercise routine completed during physical therapy exercises, enabling physiological monitoring of the patient's conditions. In exemplary embodiments, the digital physical therapy system includes a wearable inertial measurement unit (IMU), the wearable IMU attached to the patient, and configured to record three dimensional (3D) acceleration parameters, rotation measurements and tilt parameters during each of the exercise routines completed by the patient, and to store the 3D acceleration parameters, the rotation measurements, and the tilt parameters of the patient's body parts during the exercise routines completed by the patient. In exemplary embodiments, the digital physical therapy system includes one or more pressure pad sensors, one or more pressure pad sensors configured to measure weight distribution parameters of the patient's feet during the exercise routines completed by the patient; and store the weight distribution parameters of the patient's feet during the exercise routine.

In exemplary embodiments, A method of assessing neuropathy-induced balance loss and outcome of therapy, including capturing video data of a patient's body parts during exercise routines; analyzing the captured video data of the patient's body parts and generating patient motion metrics, patient posture metrics, and patient gait metrics for each exercise routine completed by the patient; storing, in a database, the generated patient motion metrics, the patient posture metrics and the patient gait metrics for each of the completed exercise routines; measuring, via a pressure sensor, weight distribution parameters of the patient's feet during the exercise routines completed by the patient and storing the weight distribution parameters in the database; measuring and mapping tremors during exercises as described and generating tremor amplitude measurements and tremor frequency measurements; and measuring and mapping patient-reported pain during the exercise routines completed by the patient and generating pain distribution measurements and pain intensity measurements and storing the pain distribution measurements and pain intensity measurements; performing a comprehensive assessment of a patient's balance and gait through analyzing the pain distribution measurements and pain intensity measurements, the tremor amplitude measurements and tremor frequency measurements, the weight distribution parameters, and the patient posture metrics and the patient gait metrics for each of the completed exercise routines; generating personalized targeted rehabilitation exercises or exercise adjustments to improve balance, coordination, and strength based on pain distribution measurements and pain intensity measurements; the tremor amplitude measurements and tremor frequency measurements; and the patient motion metrics, the patient posture metrics and the patient gait metrics; providing real-time feedback and biofeedback to the patient during the physical therapy session to guide the patient in making necessary adjustments for balance improvement, and measuring an outcome with respect to the various measurements and parameters discussed above based on the adjustments to the physical therapy sessions described above.

In exemplary embodiments, A method of audiovisual analysis of musculoskeletal disorders, including capturing, via one or more cameras or imaging devices, video data files of a patient's body and patient's joint movements during exercise routines in a physical therapy sessions; simultaneously recording sound/audio files produced by the patient's joints using a microphone system during the exercise routines; synchronizing the captured video files and the recorded sound/audio files for analysis of the patient's joints; analyzing the captured video files and audio to identify correlation between frequency, amplitude and duration of audio with respect to joint angles and position of other body parts in the captured video files; comparing correlated audio and video data of the patient with audio and video data of healthy joints utilizing machine learning algorithms to identify pathological condition data or associated musculoskeletal conditions) for the patient; storing captured synchronized audio and video data and the associated musculoskeletal conditions in patient joint database; generating recommendations for treatment of the patient's joints and the associated musculoskeletal conditions) based on analyzing and comparing steps described above; and monitoring a patient's progress during therapy sessions after implementing the generated recommendations during the therapy sessions.

In exemplary embodiments, the digital physical therapy system includes a laser-based distance measurement tool (such as LIDAR), the laser distance measurement tool configured to scan the patient's body and generate spinal contour measurements, wherein spinal machine learning algorithms are configured to analyze the spinal contour measurements to diagnose skeletal conditions like scoliosis or kyphosis. In exemplary embodiments, the digital physical therapy system includes wearable acoustic sensors or one or more microphones, the wearable acoustic sensors or microphones attached to areas near one or more joints of the patient and configured to capture audio sounds from the one or more joints during the exercise routines completed by the patient, wherein the computer-readable instructions executed by the processors or controllers include synchronized audiovisual diagnostics to analyze the captured audio sounds of the patient's joints and the video data associated with the patient's joints during movement of the patient's joints during the exercise routines completed by the patient, and to determine joint health assessment based on correlated audio sounds and video data motion patterns. In exemplary embodiments, the digital physical therapy system to include a structured illumination device, the structured illumination device to project light grid patterns onto the patient's body and the plurality of cameras to generate patterned video data or video files of the projected light grid pattern with respect to the patient's body, wherein the computer-readable instructions include perspective projection algorithms that are executable by the one or more processors to analyze the patterned video data in order to create three-dimensional (3D) image maps of the patient's body, the 3D image maps to provide detailed representations of posture and movement for comprehensive diagnostic insights and treatment planning for the patient.

In exemplary embodiments, the digital physical therapy system to utilize progressive training protocols, wherein progressive training protocols are applied in upcoming therapy sessions to adapt the upcoming exercises scheduled for the patient to gradually improve a patient's balance and coordination, and to avoid overwhelming the patient. In exemplary embodiments, the digital physical therapy system to include a a remote computing device, the remote computing device including one or more remote processors or controllers, a remote display or screen, one or more remote memory devices, and computer-readable instructions stored in the one or more remote memory devices and executable by the one or more remote processors or controllers to: a) receive the generated patient motion metrics, the generated patient posture metrics and the generated patient gait metrics; b) analyze the received patient motion metrics, the received patient posture metrics and the received patient gait metrics to track patient progress and diagnose movement disorders, and c) generate personalized, data-driven treatment plans to enhance immediate outcomes and long-term recovery from the musculoskeletal and neurological disorders for patients who cannot frequently visit a clinic. In exemplary embodiments, the digital physical therapy system to include computer-readable instructions executable by the one or more processors or controllers to perform longitudinal analysis of the stored patient motion metrics, the stored patient posture metrics and the stored patient gait metrics for all of the patient's completed physical therapy systems to support continuous tracking of patient progress, fall risk assessment, and evaluation of physical therapy treatment efficacy over time.

In exemplary embodiments, a method for detecting and quantifying tremor in patients with neurological disorders, including capturing, via an imaging system, video data files of a patient's specific body part during prescribed positions or exercises; applying motion amplification software algorithms to enhance clarity of the specific body parts in the video data files; applying edge detection to the video data files to enhance tremor object boundaries and facilitate measurement of tremor amplitude and tremor frequency; calculating tremor amplitude measurements and tremor frequency measurements based at least on the motion amplification and edge detection software algorithms application; and analyzing tremor amplitude measurements and tremor frequency measurements for diagnosis and monitoring of disorders such as Parkinson's disease and Essential Tremor.

In exemplary embodiments, a method for three-dimensional mapping of a patient, including projecting an illuminated pattern onto a patient to generate a plurality of reference lines or reference points; capturing, via one or more cameras or imaging devices, images of the patient with the illuminated pattern projected upon the patient, the images including the plurality of reference lines or reference points; retrieving focal length of the one or more cameras or imaging devices, and real world size or dimensions of the patient; measure a size of the patient in the captured images in terms of numbers of pixels; calculate real-word distances from reference areas formed by the plurality of reference lines or the plurality of reference points of the patient to the one or more cameras or imaging device using perspective projection techniques or algorithms; generate three-dimensional maps of the patient for use in providing precises diagnostics and continuous monitoring of the patient; and store the generated three-dimensional maps of the patient in the patient mapping coordinate database.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step. In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

As used herein, the term "or" is used inclusively to refer items in the alternative and in combination.

As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A digital physical therapy system for diagnosing, treating, and rehabilitating patients with musculoskeletal and neurological disorders, comprising:
 a plurality of cameras configured to capture video data of a patient's body parts during exercise routines and configured to capture additional video data of specific patient's body parts in prescribed positions during each exercise routine;
 one or more processors or controllers;
 one or more memory devices; and
 computer-readable instructions stored in the one or more memory devices, and executable by the one or more processors or controllers, the computer-readable instructions including machine learning algorithms to analyze the captured video data of the patient's body parts and to generate patient motion metrics, patient posture metrics, and patient gait metrics for each exercise routine completed by the patient based on the analyzed video data;

store, in a database, the generated patient motion metrics, the patient posture metrics and the patient gait metrics for each of the completed exercise routines;

wherein the generated patient motion metrics, the generated patient posture metrics and the generated patient gait metrics are used to track patient progress during physical therapy sessions, diagnose movement disorders, and provide personalized, data-driven treatment plans to enhance immediate outcomes and long-term recovery with respect to the musculoskeletal and neurological disorders;

apply motion amplification algorithms to enhance the additional video data to provide clarity of tremor movements;

apply edge detection algorithms to enhance tremor movement boundaries and detection;

generate tremor amplitude measurements and tremor frequency measurements based on the motion amplification and edge detection algorithms; and store, in the database, the generated tremor amplitude measurements and tremor frequency measurements, wherein the generated tremor amplitude measurements and tremor frequency measurements are analyzed.

2. The system of claim 1, further comprising wearable surface electromyography (sEMG) sensors, the wearable sEMG sensors attached to the patient and configured to measure muscle activation pattern parameters, and store the muscle activation pattern parameters in the database, wherein the muscle activation pattern parameters provide biofeedback to optimize therapeutic interventions based on muscular contributions to posture and movement of the patient.

3. The system of claim 1, further comprising wearable oximetry sensors, the wearable oximetry sensors attached to the patient, and configured to capture heart rate measurements, blood oxygen levels and $CO_2$ levels, and to store the heart rate measurements, the blood oxygen levels, and the $CO_2$ levels in real-time during each exercise routine completed during the physical therapy sessions, enabling physiological monitoring of the patient's condition.

4. The system of claim 1, further comprising a wearable inertial measurement unit (IMU), the wearable IMU attached to the patient, and configured to record three dimensional (3D) acceleration parameters, rotation measurements and tilt parameters during each of the exercise routines completed by the patient, and to store the 3D acceleration parameters, the rotation measurements, and the tilt parameters of the patient's body parts during the exercise routines completed by the patient.

5. The system of claim 1, further comprising a pressure pad, the pressure pad configured to measure weight distribution parameters of the patient's feet during the exercise routines completed by the patient; and store the weight distribution parameters of the patient's feet during the exercise routines.

6. The system of claim 5, the computer-readable instructions executable by the one or more processors or controllers to:

measure and map patient-reported pain during the exercise routines completed by the patient and generating pain distribution measurements and pain intensity measurements and storing the pain distribution measurements and pain intensity measurements;

perform a comprehensive assessment of a patient's balance and gait through analyzing the pain distribution measurements and pain intensity measurements, the tremor amplitude measurements and tremor frequency measurements, the weight distribution parameters, and the patient posture metrics and the patient gait metrics for each of the completed exercise routines;

generate personalized targeted rehabilitation exercises or exercise adjustments to improve balance, coordination, and strength based on the pain distribution measurements and pain intensity measurements; the tremor amplitude measurements and tremor frequency measurements; and the patient motion metrics, the patient posture metrics and the patient gait metrics; and provide real-time feedback and biofeedback to the patient during the physical therapy session to guide the patient in making necessary adjustments for balance improvement.

7. The system of claim 1, further comprising a laser-based distance measurement tool, the laser distance measurement tool configured to scan the patient's body and generate spinal contour measurements, wherein spinal machine learning algorithms are configured to analyze the spinal contour measurements.

8. The system of claim 1, further comprising wearable acoustic sensors or microphones, the wearable acoustic sensors or the microphones attached to areas near one or more joints of the patient and configured to capture audio sounds from the one or more joints during the exercise routines completed by the patient, wherein the computer-readable instructions executed by the processors or controllers include synchronized audiovisual diagnostics to analyze the captured audio sounds of the patient's joints and the video data associated with the patient's joints during movement of the patient's joints during the exercise routines completed by the patient, and to determine joint health assessment based on correlated audio sounds and video data motion patterns.

9. The system of claim 1, further comprising a structured illumination device, the structured illumination device to project light grid patterns onto the patient's body and the plurality of cameras to generate patterned video data or video files of the projected light grid pattern with respect to the patient's body, wherein the computer-readable instructions include perspective projection algorithms that are executable by the one or more processors to analyze the patterned video data or video files in order to create three-dimensional (3D) image maps of the patient's body, the 3D image maps to provide detailed representations of posture and movement for comprehensive diagnostic insights and treatment planning for the patient.

10. The system of claim 1, wherein progressive training protocols are applied in upcoming therapy sessions to adapt upcoming exercises scheduled for the patient to gradually improve a patient's balance and coordination, and to avoid overwhelming the patient.

11. The system of claim 1, further comprising a remote computing device, the remote computing device including one or more remote processors or controllers, a remote display or screen, one or more remote memory devices, and computer-readable instructions stored in the one or more remote memory devices and executable by the one or more remote processors or controllers to: a) receive the generated patient motion metrics, the generated patient posture metrics and the generated patient gait metrics; b) analyze the received patient motion metrics, the received patient posture metrics and the received patient gait metrics to track patient progress, and c) generate the personalized, data-driven treatment plans to enhance the immediate outcomes and the long-term recovery from the musculoskeletal and neurological disorders for patients who cannot frequently visit a clinic.

12. The system of claim 1, the computer-readable instructions executable by the one or more processors or controllers to perform longitudinal analysis of the stored patient motion metrics, the stored patient posture metrics and the stored patient gait metrics for all of the patient's completed physical therapy systems to support continuous tracking of patient progress, fall risk assessment, and evaluation of physical therapy treatment efficacy over time.

13. A method of using a digital physical therapy system for diagnosing, treating, and rehabilitating patients with musculoskeletal and neurological disorders, comprising:
    capturing, via one or more cameras, video data of a patient's body parts during exercise routines;
    capturing, via the one or more cameras, additional video data of specific patient's body parts in prescribed positions during each exercise routine;
    utilizing machine learning algorithms to analyze the captured video data of the patient's body parts and to generate patient motion metrics, patient posture metrics, and patient gait metrics for each exercise routine completed by the patient based on the analyzed video data;
    storing, in a database, the generated patient motion metrics, the patient posture metrics and the patient gait metrics for each of the completed exercise routines,
    wherein the generated patient motion metrics, the generated patient posture metrics and the generated patient gait metrics are used to track patient progress during physical therapy sessions, diagnose movement disorders, and provide personalized, data-driven treatment plans to enhance immediate outcomes and long-term recovery with respect to the musculoskeletal and neurological disorders;
    applying motion amplification algorithms to enhance the additional video data of the specific patient's body parts to provide clarity of tremor movements;
    applying edge detection processes to the additional video data to enhance tremor movement boundaries and detection;
    generating tremor amplitude measurements and tremor frequency measurements based on the motion amplification algorithm and edge detection processes;
    storing, in the database, the generated tremor amplitude measurements and tremor frequency measurements, wherein the generated tremor amplitude measurements and tremor frequency measurements are analyzed; and
    scanning the patient's body utilizing a laser-distance measurement tool and generate spinal contour measurements, wherein spinal machine learning algorithms are configured to analyze the spinal contour measurements.

14. The method of claim 13, further comprising:
receiving muscle activation pattern parameters from one or more sEMG sensors attached to the patient and storing the muscle activation pattern parameters in the database, wherein the muscle activation pattern parameters provide biofeedback to optimize therapeutic interventions based on muscular contributions to posture and movement of the patient.

15. The method of claim 13, further comprising:
capturing heart rate measurements, blood oxygen levels and $CO_2$ levels via one or more wearable oximetry sensors, and
storing the heart rate measurements, the blood oxygen levels and the $CO_2$ levels in the database in real-time during each exercise routine completed during physical therapy exercises, enabling physiological monitoring of the patient's condition.

16. The method of claim 13, further comprising:
recording, via a wearable inertial measurement unit (IMU) attached to the patient, three dimensional (3D) acceleration parameters, rotation measurements and tilt parameters of a patient's body parts during each of the exercise routines completed by the patient, and
storing the 3D acceleration parameters, the rotation measurements, and the tilt parameters of the patient's body parts during the exercise routines completed by the patient.

17. The method of claim 13, further comprising:
measuring, via a pressure pad, weight distribution parameters of a patient's feet during the exercise routines completed by the patient; and
storing the weight distribution parameters of the patient's feet during the exercise routine.

18. The method of claim 13, further comprising:
projecting, via a structured illumination device, light grid patterns onto the patient's body, and
generating, via the plurality of cameras, patterned video data or video files of the projected light grid pattern with respect to the patient's body; and
analyzing the patterned video data or video files in order to create three-dimensional (3D) image maps of the patient's body, the 3D image maps to provide detailed representations of posture and movement for comprehensive diagnostic insights and treatment planning for the patient.

* * * * *